(12) United States Patent
Ho et al.

(10) Patent No.: US 8,028,699 B2
(45) Date of Patent: *Oct. 4, 2011

(54) FULL FACE RESPIRATORY MASK WITH INTEGRATED NASAL INTERFACE

(75) Inventors: Peter Chi Fai Ho, Pittsburgh, PA (US); Jason P. Eaton, Hunker, PA (US)

(73) Assignee: Ric Investments, LLC, Wilmington, DE (US)

( * ) Notice: Subject to any disclaimer, the term of this patent is extended or adjusted under 35 U.S.C. 154(b) by 202 days.

This patent is subject to a terminal disclaimer.

(21) Appl. No.: 12/256,059

(22) Filed: Oct. 22, 2008

(65) Prior Publication Data
US 2009/0038619 A1   Feb. 12, 2009

Related U.S. Application Data

(63) Continuation of application No. 11/633,888, filed on Dec. 5, 2006, now Pat. No. 7,448,386.

(60) Provisional application No. 60/748,311, filed on Dec. 7, 2005.

(51) Int. Cl.
*A62B 18/02* (2006.01)
(52) U.S. Cl. .............................. 128/206.21; 128/205.25
(58) Field of Classification Search ............. 128/207.18, 128/205.25, 206.21, 206.28, 207.11, 207.14
See application file for complete search history.

(56) References Cited

U.S. PATENT DOCUMENTS

| | | | |
|---|---|---|---|
| 4,263,908 A | 4/1981 | Mizerak | |
| 4,971,451 A | 11/1990 | Hori | |
| 5,243,971 A | 9/1993 | Sullivan | |
| 5,348,981 A | 9/1994 | Moore | |
| 5,647,355 A | 7/1997 | Starr | |
| 5,647,357 A | 7/1997 | Barnett | |
| 5,884,624 A | 3/1999 | Barnett | |
| 6,397,847 B1 | 6/2002 | Scarberry | |
| 6,418,928 B1 | 7/2002 | Bordewick | |
| 6,805,117 B1 | 10/2004 | Ho | |
| 6,851,425 B2 | 2/2005 | Jaffre et al. | |
| 6,860,269 B2 | 3/2005 | Kwok | |
| 6,895,965 B2 | 5/2005 | Scarberry | |
| 7,066,179 B2 | 6/2006 | Eaton | |
| 7,069,932 B2 | 7/2006 | Eaton | |
| 7,448,386 B2 * | 11/2008 | Ho et al. | ........... 128/206.21 |
| 2006/0130844 A1 | 6/2006 | Ho | |
| 2006/0225740 A1 | 10/2006 | Eaton | |
| 2007/0107733 A1 | 5/2007 | Ho | |

OTHER PUBLICATIONS

Peter Ho et al., "Exhalation Port with Built-In Entertainment Valve Feature" Pending U.S. Appl. No. 11/312,027, filed Oct. 20, 2005.

* cited by examiner

*Primary Examiner* — Steven Douglas
(74) *Attorney, Agent, or Firm* — Michael W. Haas

(57) ABSTRACT

A patient interface that reliably and comfortably seals a user's face by providing an oral-nasal mask that includes an integrated nasal interface. The patient interface includes a seal member having an oral cushion portion configured to surround the user's mouth and a nasal interface portion that provides an interface with the user's nose. The seal member, including the oral cushion portion and the nasal interface portion, is a unitary member. Finally, the nasal interface portion remains below the bridge of the nose.

20 Claims, 44 Drawing Sheets

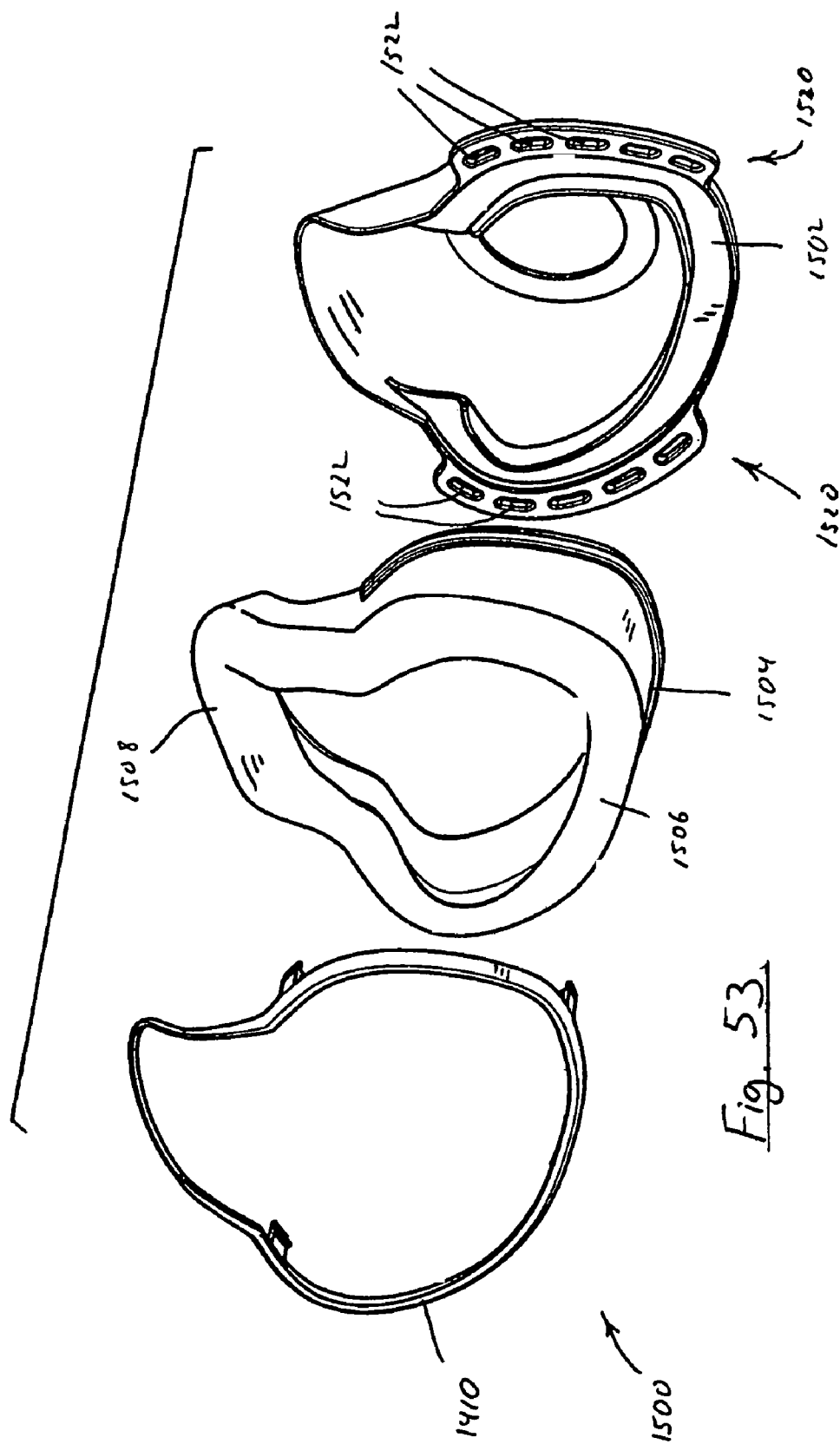

FULL FACE RESPIRATORY MASK WITH INTEGRATED NASAL INTERFACE

CROSS-REFERENCE TO RELATED APPLICATIONS

This application claims priority under 35 U.S.C. §119(e) from provisional U.S. patent application No. 60/748,311, filed Dec. 7, 2005, the contents of which are incorporated herein by reference.

BACKGROUND OF THE INVENTION

1. Field of the Invention

The present invention relates, in general, to a full face mask that provides a sealed interface with the nose and mouth of a user, and, in particular, to a full face mask having an oral cushion portion that seals generally around the mouth and a nasal interface portion that seals generally at or around the nares and remains below the bridge of the nose.

2. Description of the Related Art

A variety of respiratory masks are known that have flexible seals, cover a portion of a user's face, and are designed to create a seal against the user's face. Because of the sealing effect that is created, gases can be provided at a positive pressure within the mask for consumption by the user. The uses for such masks range from high altitude breathing, i.e., aviation applications, to mining and fire fighting applications, to various medical diagnostic and therapeutic applications. For example, such masks are used in the delivery of continuous positive airway pressure (CPAP) or variable airway pressure, which varies with the user's respiratory cycle or which varies with the condition of the user, to treat a medical disorder, such as sleep apnea syndrome, obstructive sleep apnea (OSA), congestive heart failure, and cheynes-stokes respiration.

A requisite of such respiratory masks is that they provide an effective seal against the user's face to prevent leakage of the gas being supplied. Commonly, in prior mask configurations, a good mask-to-face seal has been attained in many instances only with considerable discomfort to the user. This problem is most crucial because such masks are typically worn for an extended period of time. One concern in such a situation is that a user may avoid wearing an uncomfortable mask, defeating the purpose of the prescribed pressure support therapy.

A wide variety of patient interfaces are known, including nasal masks that cover only the nose, nasal canulas or prongs that fit into the nares of the user, total face masks that cover a majority of the user's face, oral-nasal or full face masks that cover the nose and mouth area, among other variations.

Traditional oral-nasal masks cover the entire nose and mouth area of the user. Due to their size and bulk, they may be less comfortable and more intrusive than other masks. Some users may resist the wearing of oral-nasal masks due to physiological reasons, such as claustrophobia or clithrophobia (fear of being enclosed). Oral-nasal mask are typically heavy and bulky, may interfere with a user's facial comfort, and may not facilitate the wearing of eyeglasses. Some oral-nasal masks may irritate a user's nose bridge, which typically is an area of thin skin, where even slight pressure can cause a blood flow constriction, and, hence, skin breakdown and/or discomfort.

It can be difficult to achieve a good seal in typical oral-nasal masks due to the large and varied area being covered. This area includes the area around the mouth, the front of the face from the ends of the mouth to the nose, and the nose itself, including the bridge. The variations in contour and size from nose to mouth are much greater than those among the nose or among the mouth alone.

Another disadvantage of conventional masks is the forehead support. Typically, forehead supports stabilize the mask system as well as providing pressure point relief. The forehead support, however, is often the source of pressure point and skin break down.

SUMMARY OF THE INVENTION

Accordingly, it is an object of the present invention to provide a patient interface that overcomes the shortcomings of conventional oral-nasal masks. This object is achieved according to one embodiment of the present invention by providing a patient interface that includes a faceplate and a seal member coupled to the faceplate. The seal member contacts the user's face to provide a sealed interface with the user. The seal member includes an oral cushion portion and a nasal interface portion. The oral cushion portion provides a sealed interface with the user over a sealing area that at least partially surrounds the user's mouth. The nasal interface portion is integral with the oral cushion portion and contacts at least a portion of the user's nose below the bridge of the nose. The nasal interface portion provides a sealed interface with a surface of such a user proximate to the nares of such a user. The patient interface having this configuration provides a contacting area on the user's face that is less than conventional oral-nasal masks and also reduces the complexity of sealing, because both the sealing surface and the variation among the surfaces is reduced.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 53 is an exploded view of the patient interface of FIG. 51.

DETAILED DESCRIPTION OF THE EXEMPLARY EMBODIMENTS

Figure 1:
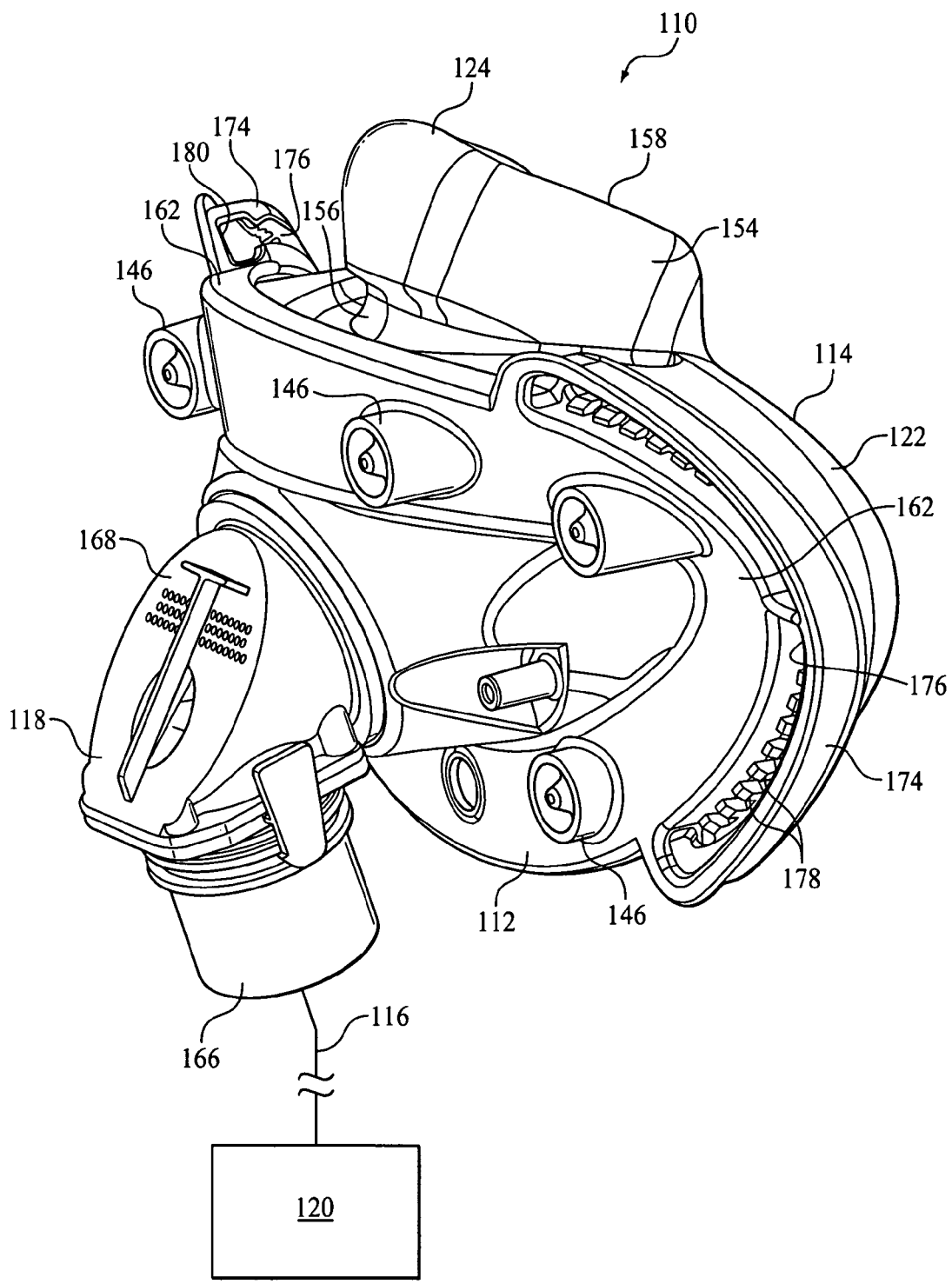
FIG. 1 is a perspective view of a first embodiment of a patient interface according to the principles of the present invention shown schematically coupled to a pressure generating system.
Figure 2:
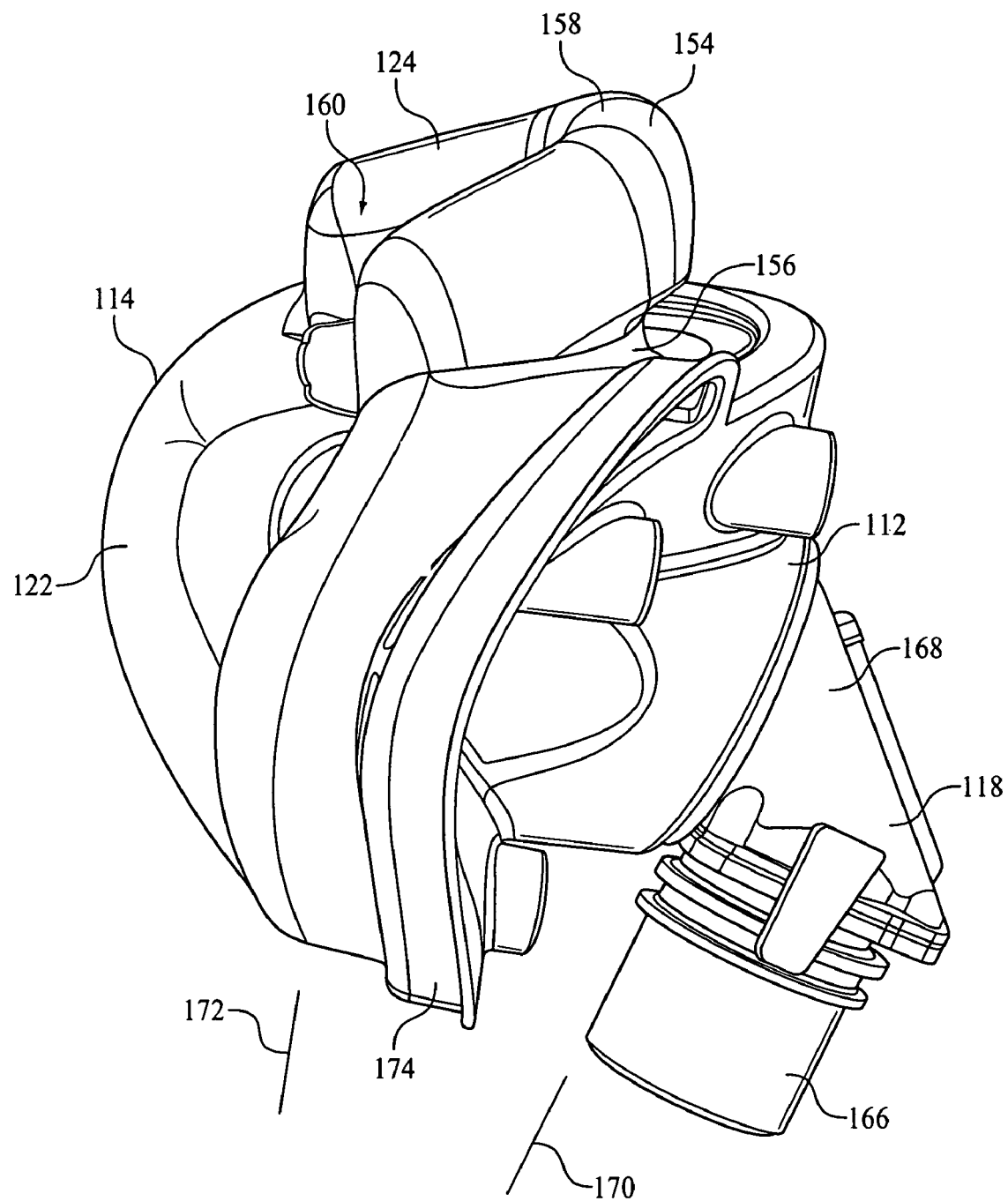
FIG. 2 is a side view of the patient interface of FIG. 1.
Figure 3:
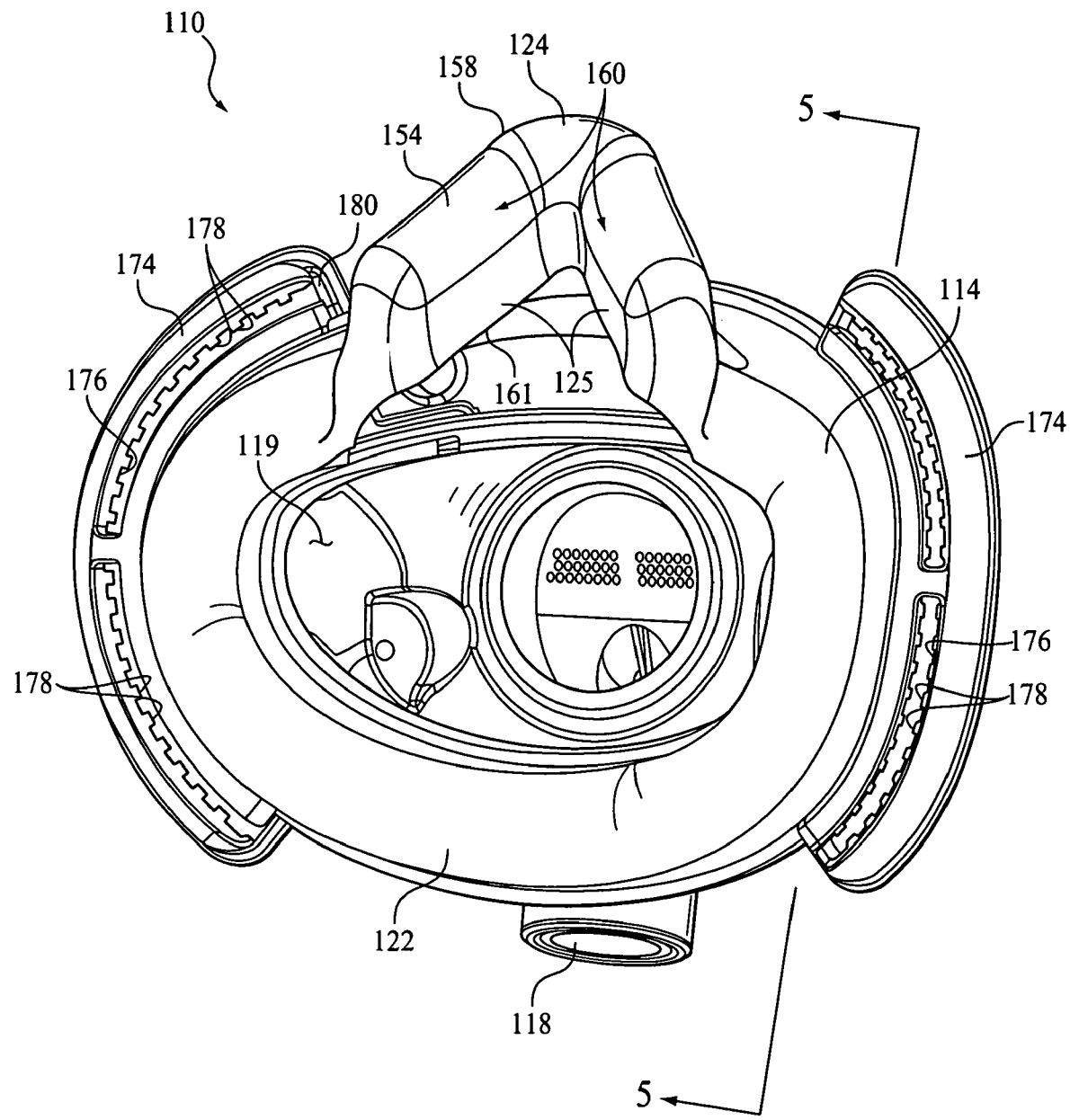
FIG. 3 is a rear view of the patient interface of FIG. 1.

FIGS. 1-5 represent a first exemplary embodiment of a patient interface 110 according to the principles of the present invention. Patient interface 110 includes a faceplate 112 and a seal member 114 attached to faceplate 112 for contacting the user's face. Faceplate 112 has a user side to which a seal member 114 is attached, and an exterior side, opposite the user side, and adapted for receiving a supply of pressurized breathing gas. A conduit 116 is connected to the exterior side of faceplate 112 via a patient interface coupling 118. Conduit 116, which is typically a flexible tube and is known in the art as a "patient circuit", delivers gas produced by a pressure generating device 120 to patient interface 110. An opening 117 is provided in the faceplate to communicate a flow of gas between a chamber 119 defined in the patient interface and conduit 116.

The present invention contemplates that pressure generating device 120 is any conventional ventilation or pressure support system. Examples of such pressure support systems include, but are not limited to: a ventilator, continuous positive airway pressure (CPAP) device, or a variable pressure device, e.g. an auto-titrating device in which the pressure varies with the condition of the user, such as whether the user is snoring, experiencing an apnea, hyponea, or upper airway resistance. Still other examples of pressure support systems include a proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device.

Patient interface 110 of the present invention is an oral-nasal mask constructed to interface with both the user's nose and mouth. Masks that interface with the nose and mouth simultaneously are also known as full face masks. Seal member 114, which is also referred to as a cushion, is configured to surround the user's mouth while also providing an integrated, one-piece unitary interface with the user's nose. In the embodiment shown in FIGS. 1-5, seal member 114 is a unitary member that includes an oral cushion portion 122 and a nasal interface portion 124. Oral cushion portion 122 provides a sealed interface with the over a sealing area that at least partially surrounds the user's mouth. Nasal interface portion 124 is integral with oral cushion portion 122 and contacts at least a portion of a nose of the user below the bridge to provide a sealed interface with the surface of the user proximate to the nares. That is the present invention contemplates that the nasal interface portion contacts the nose, including extending over the tip of the nose and extending up the nose, but not so high so to cover the bridge of the nose.

Figure 31:
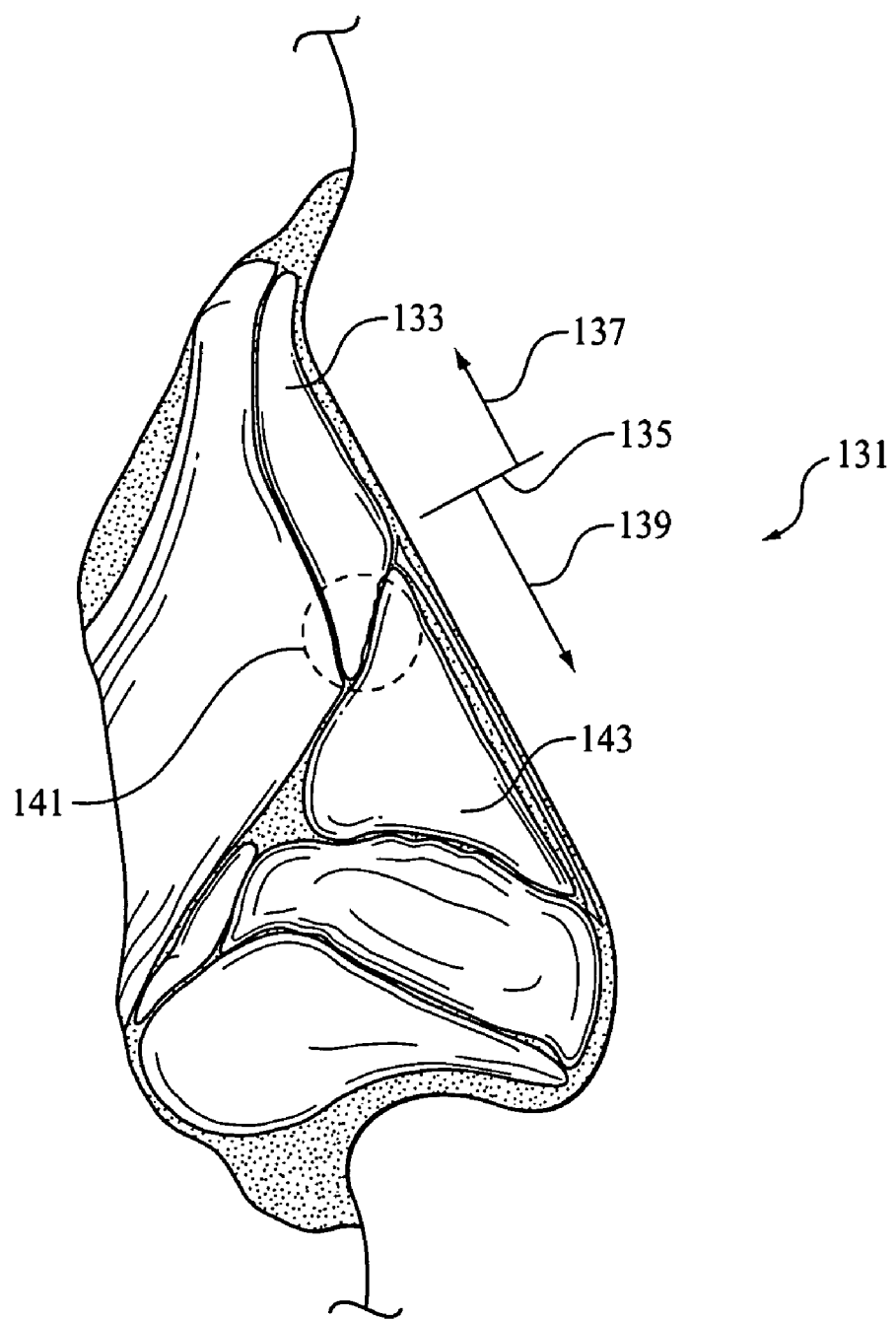
FIG. 31 is a side view of a human nose illustrating the various anatomical features and the location on the nose for the nasal interface portion of the seal member according to the principles of the present invention.

To better understand where the present invention contemplates that the nasal interface portion of the seal member contacts the user, FIG. 31 is provided, which illustrates the anatomical features of a human nose 131. As shown in this figure, the human nose includes a nasal bone 133 that extends from between the eyes (not shown), toward the mouth, and terminates somewhere above or near the middle of the nose. The termination point of the nasal bone is indicated by line 135. Above line 135, as indicated by arrow 137, is the nasal bone, and below line 135, as indicated by arrow 139, is the cartilage of septum. In referring to the "bridge of the nose", the present invention is referring portion of the nose where the nasal bone lies with respect to the midline of the nose, i.e., the portion of the nose above line 135, as indicated by arrow 139, along the ridge of the nose.

Thus, in describing the nasal interface portion of the seal member of the present invention as contacting the user below the bridge of the nose, the present invention is referring to a seal having a user contacting area that is at or below line 135 (the end of the nasal bone), as indicated by arrow 139, with respect to the mid-line of the nose. The present invention contemplates that the contacting area of the nasal interface portion can extend along the flanks of the nose, so long as the sealing area remains below line 135, even if the seal member overlies the nasal bone on the side of the nose, such as at area 141. However, in an exemplary embodiment of the present invention, the nasal interface portion of the seal member this invention rests on and seals against the soft tissue around the lower portion of the lateral cartilage of the nose on the nasal septum, as indicated by area 143.

Seal member 114 is preferably formed from a flexible material such as silicone. Seal member 114 provides a seal that minimizes contact with the user's face by integrating a tip-of-the-nose or nostril seal with a mouth cushion, which, in an exemplary embodiment, is oval-shaped and only circles the mouth and remain below the bridge of the nose. Thus, the seal member of the present invention limits contour variation, such as the variation of the nose to mouth transition, thereby making it easier to provide an effective seal with the surface of the user, which ultimately maximizes patient comfort and compliance with the prescribed pressure support therapy.

The present invention contemplates that the faceplate and the seal member, including the oral cushion portion and the nasal interface portion, can have a variety of configurations. Many of these possible alternative configurations are illustrated in the attached figures and described below. A first embodiment for the faceplate and seal member according to the principles of the present invention shown in FIGS. 1-5 will now be described.

Figure 4:
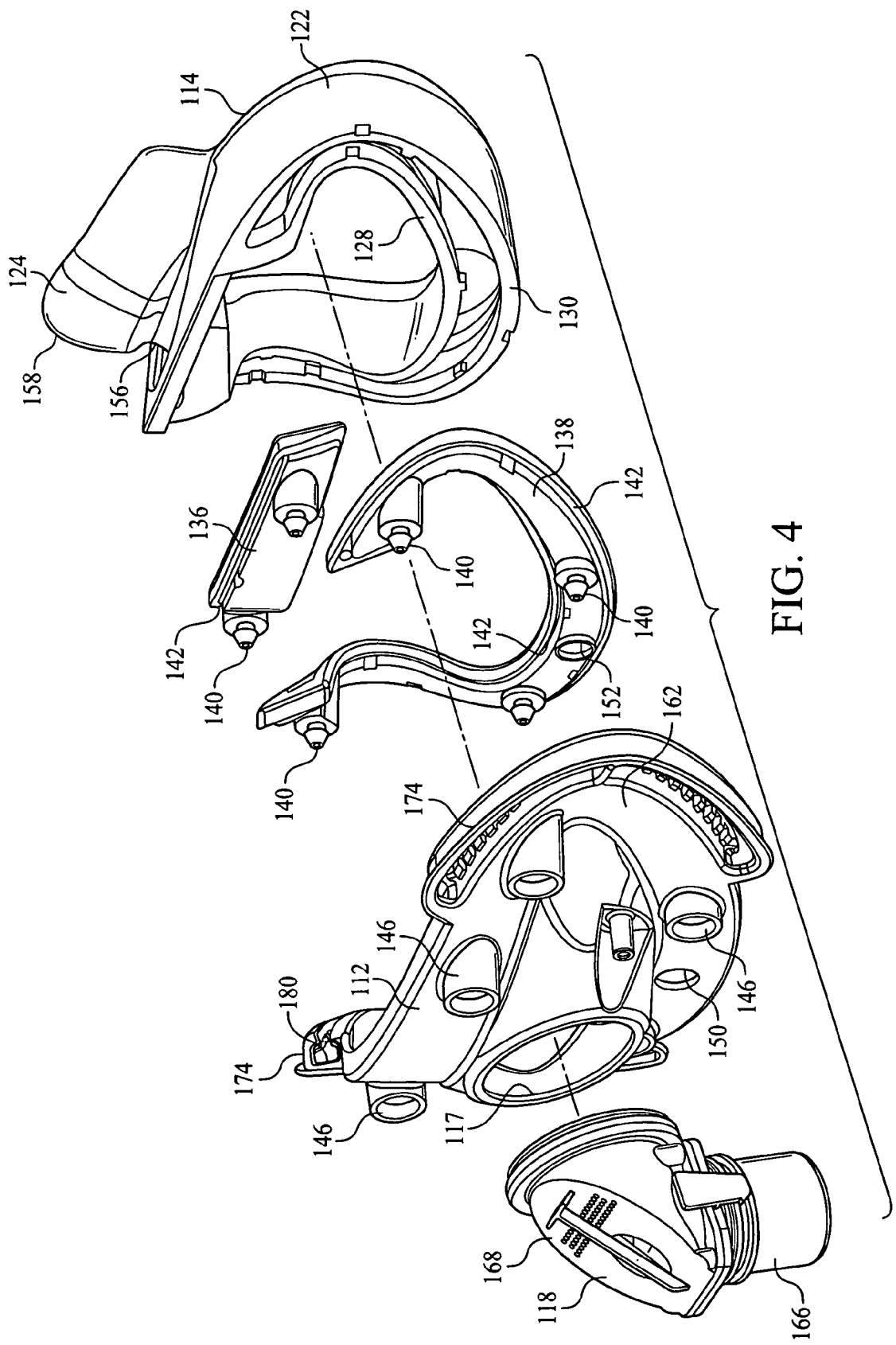
FIG. 4 is an exploded view of the patient interface of FIG. 1.
Figure 5:
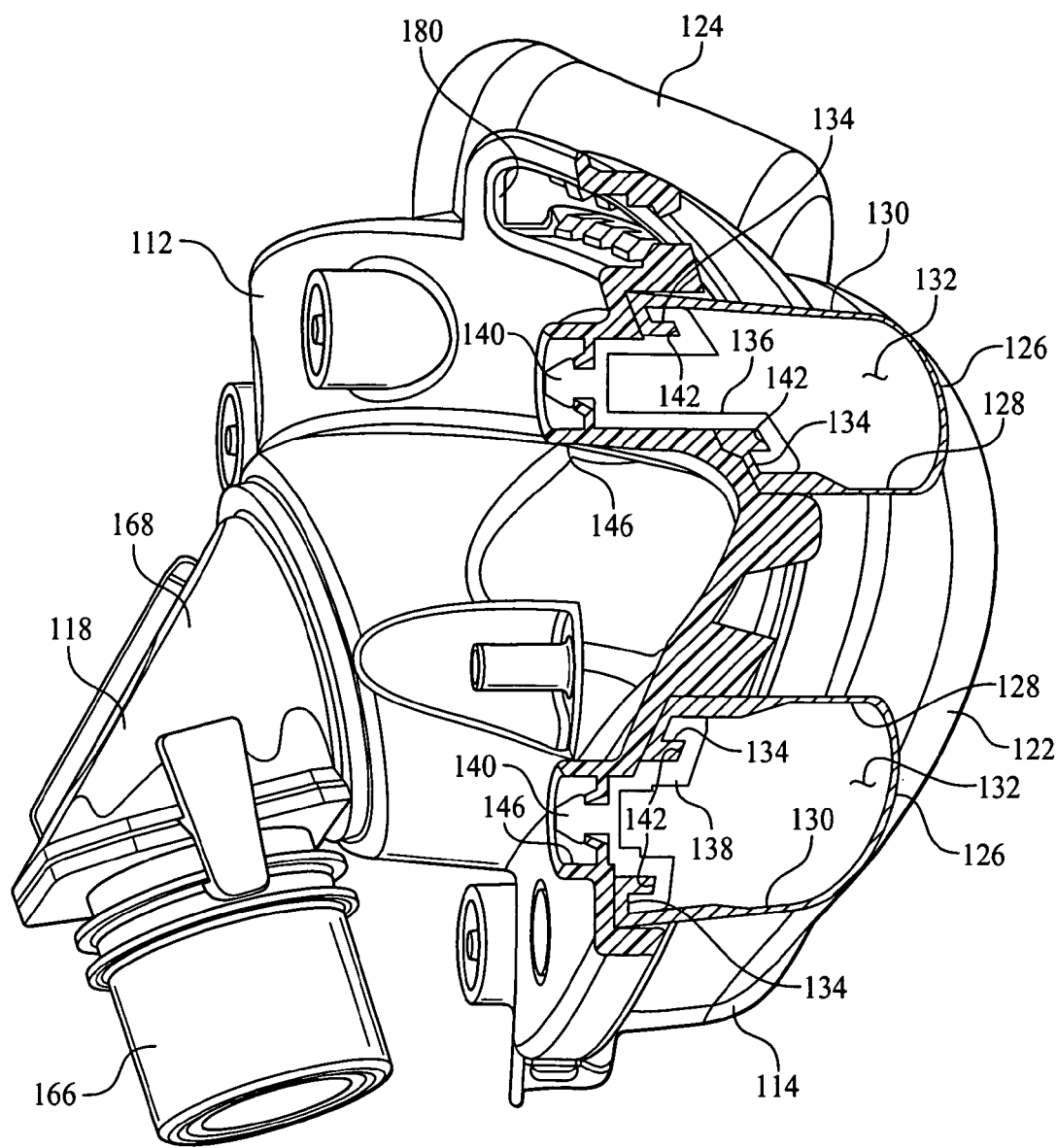
FIG. 5 is a cross-sectional view of the patient interface of FIG. 1 taken along line 5-5 of FIG. 3.

As can perhaps best be seen in FIGS. 4-5, oral cushion portion 122 is a gas-filled cushion having a U-shaped cross section. An exemplary embodiment of a gas-filled cushion suitable for use in the present invention is disclosed in co-pending provisional U.S. patent application Ser. No. 11/599, 133, ("the '133 application") the contents of which are incorporated herein by reference.

Oral cushion portion includes a curved portion 126, an inner side wall 128, an outer side wall 130, and an interior 132. Oral cushion portion 122 is preferably formed from liquid injection molded silicone, but could be formed from other suitable materials. Oral cushion portion 122 has a varied wall thickness as shown in FIG. 5. However, the present invention also contemplates the oral cushion portion 122 can have a uniform wall thickness. The inner and outer side walls 128, 130 of oral cushion portion 122 have interiorly disposed, U-shaped grooves 134 at their ends opposite curved portion 126.

To mount seal member 114 to faceplate 112, oral cushion portion 122 is coupled to a two-piece base or mounting ring 136, 138. Two-piece base or mounting ring Upper mounting portion 136 and lower mounting portion 138 are assembled with oral cushion portion 122. In the illustrated embodiment, lower mounting portion 138 cooperates with oral cushion portion 122 to seal the open end of interior 132 forming a sealed gas-filled chamber corresponding to interior 132. In this embodiment, the oral cushion portion is configured such that the oral cushion portion extends around the mouth but is not located at the portion of the oral cushion portion underlying the nose. Upper mounting portion 136 cooperates with the portion of oral cushion portion 122 that cooperates with or forms nasal interface portion 124 to the nasal interface portion of the seal member to faceplate 112. Snapping members 140 are inserted into corresponding mounting members 146 on faceplate 112. It is to be understood that the present invention contemplates using other suitable assemblies to attach seal member 114 to faceplate 112 in this or any of the other embodiments.

In the illustrated embodiment, gas-filled chamber 132 is inflated or deflated through a valve (not illustrated in FIGS. 1-5, see valve 450 in FIGS. 15-17) incorporated in faceplate 112. The valve cooperates with gas-filled chamber 132 through a hole 150 in faceplate 112 and a corresponding hole 152 in lower mounting portion 138. The valve may be syringe or a manually operated gas blowing device. Of course, the present invention contemplates eliminating the valve in favor of a fixed volume of gas in interior 132 of seal member 114.

If chamber 132 is filled from the ambient atmosphere, the gas in the chamber is typically air. However, the present invention contemplates that the gas in chamber 132 can be any suitable gas or gas mixture. In addition, the present invention contemplates that chamber 132 can be filled with any suitable material in addition to or in place of gas, such as fluid, gel, foam, or any combination thereof. Examples of suitable gel materials are disclosed in U.S. Pat. Nos. 5,647,357 and 5,884,624 the contents of which are incorporated hereby by reference. The present invention also contemplates that the material in oral cushion portion 122 can be a material that can be shaped and maintain the new shape. Examples of suitable gel materials that have shape retention properties are disclosed in U.S. Pat. Nos. 6,397,847 and 6,895,965 the contents of which are incorporated hereby by reference.

The present invention also contemplates providing an optional pressure release valve to regulate the level of inflation of the seal member or portions thereof through the control of internal pressure to enhance comfort. The valve provides an upper limit to the pressure inside the air-filled chamber. When the mask is strapped on a user's face, air is displaced such that internal pressure increases inside the gas-filled chamber. Once the internal pressure exceeds the pre-set value, the release valve opens and lets excessive air out, thus, reducing strapping and pressure points.

Oral cushion portion 122 surrounds the mouth of the user forming a sealing interface therewith. Nasal interface portion 124 extends from the top of oral cushion portion 122 and has generally V-shaped contour sides 125 that wrap around the sides of the user's nose (see FIG. 3). Nasal interface portion 124 has a relatively low profile so that it does not come in contact with the bridge of the user's nose. Nasal interface portion 124 is bounded at its upper extremity by the lower end of the user's nose including the tip and lateral flanks thereof. In the illustrated exemplary embodiment, nasal interface portion 124 is formed from a flexible peripheral wall 154, which has a base 156 integral with cushion flap portion 122 and an outer contoured portion 158. Extending from outer contoured portion 158 is an in-turned surface 160 for contacting the user's nose. Nasal interface portion 124 forms an interface that is open to the pressurized interior (chamber 119) of the patient interface via notched opening 161. Because the highest point of the patient interface remains below the bridge of the nose when in use, the user is able to wear glasses and easily access his or he eyes while the patient interface is being worn.

Faceplate 112 has a generally oval shape that is contoured to the face of a user such that ends 162 of the oval wrap around the sides of the user's face on either side of the user's mouth. Faceplate 112 is a member formed from a rigid or semi-rigid plastic, such as Polycarbonate. However, the present invention also contemplates that the faceplate can be formed from other materials, such as cloth or other fabric, or an elastomer, or any combination thereof. Thus, the faceplate can be a flexible member.

Faceplate 112 has a generally circular opening 117 to which coupling 118 is rotatably attached. Coupling 118 has a conduit connection portion 166 and an exhalation/entrainment valve portion 168. In conventional masks, the circular opening for attachment of the conduit coupling typically lies in a plane that is perpendicular to the seal member. In the present invention, opening 117 lies in a plane, as generally indicated by line 170 in FIG. 2, that is at an angle with respect to the plane of seal member 114, as generally indicated by line 172. These two planes are angled with respect to on another because when patient interface 110 is donned by the user, the upper portion of the patient interface (namely the nasal interface portion) will be moved toward the user further than the lower portion. The angle between planes 170 and 172 ensures that conduit connection portion 166 is disposed at angle that more in line with the typical position of conduit 116 in a conventional oral-nasal mask.

Patient interface 110 is held in place on a user's face by a headgear, examples of which are shown in FIGS. 27-30 and discussed below. The headgear includes straps that attach to the patient interface. The present invention contemplates that any technique for attaching the headgear straps to the patient interface can be used in the patient interface of the present invention. One embodiment is discussed below and is also disclosed in the '133 application. It is to be understood that any other headgear attachment technique is contemplated by the present invention. For example, U.S. Pat. Nos. 7,066,179 ("the '179 patent") and 7,069,932 ("the '932 patent"), and in U.S. patent application Ser. No. 11/449,111 (publication no. 2006 0225740) ("the '111 application"), the contents of each of which are incorporated herein by reference, discloses a ball-and-socket and other headgear attachment technique suitable for use with the patient interface of the present invention.

To attach the headgear straps to faceplate 112, attachment rails 174 provided on each end of the faceplate. Each attachment rail includes multiple position slots 176 for receiving a stem of a headgear attachment clip (see headgear clip 914 in FIG. 27) attached to a headgear straps. Each slot includes a plurality of notches 178 and detents (areas between adjacent notches) so that the stem or other portion of the headgear attachment clip can rest at a particular location along the length of each slop. Openings 180 are provided at the ends of rails 174 to allow the stem to be inserted into slots 176.

The headgear may be releasably attached to patient interface 110 at either two points or four points corresponding to two or four slots on the mask. This provides a multiple position anchoring option for the user to improve and customize attachment stability, thus, eliminating the need for a forehead support and allows for stability even when using only a two point attachment arrangement. Also, because the mask does not extend as high on the face as a conventional oral-nasal mask, no attachment point is needed near the eyes or upper nose. It is to be understood, however, that the present invention contemplates using any conventional connection assembly to attach a headgear to faceplate 112 in this or any of the other embodiments.

The present invention contemplates the headgear that can be used with respiratory mask 110 can be any suitable headgear, i.e., any conventional headgear used in the patient interface field. For example, a typical headgear assembly comprises a headpiece that overlies a portion of the user's crania and with headgear straps extending therefrom to adjustably connect the headgear to the mask.

Alternative exemplary embodiments of the patient interface, i.e., respiratory mask, of the present invention are illustrated in FIGS. 6-22. In these embodiments, many features are similar to those illustrated in FIGS. 1-5. Thus, the description of this embodiment will focus primarily on the features unique to each embodiment. It is to be understood, however, that the present invention contemplates other configurations for the present invention and mixing and matching of the features of the elements illustrated in all of these embodiments.

Figure 6:
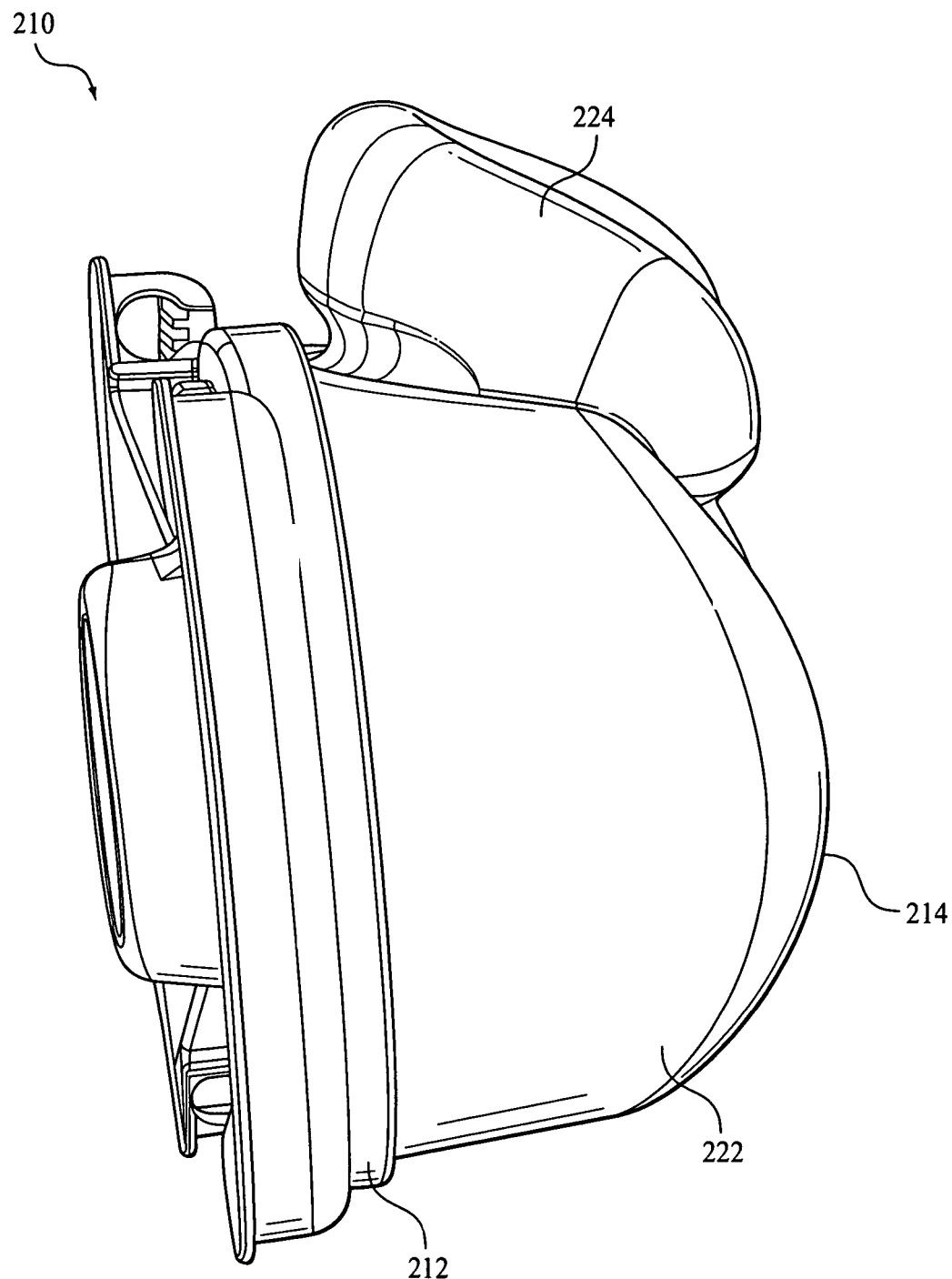
FIG. 6 is a side view of a second embodiment of a patient interface according to the principles of the present invention.
Figure 7:
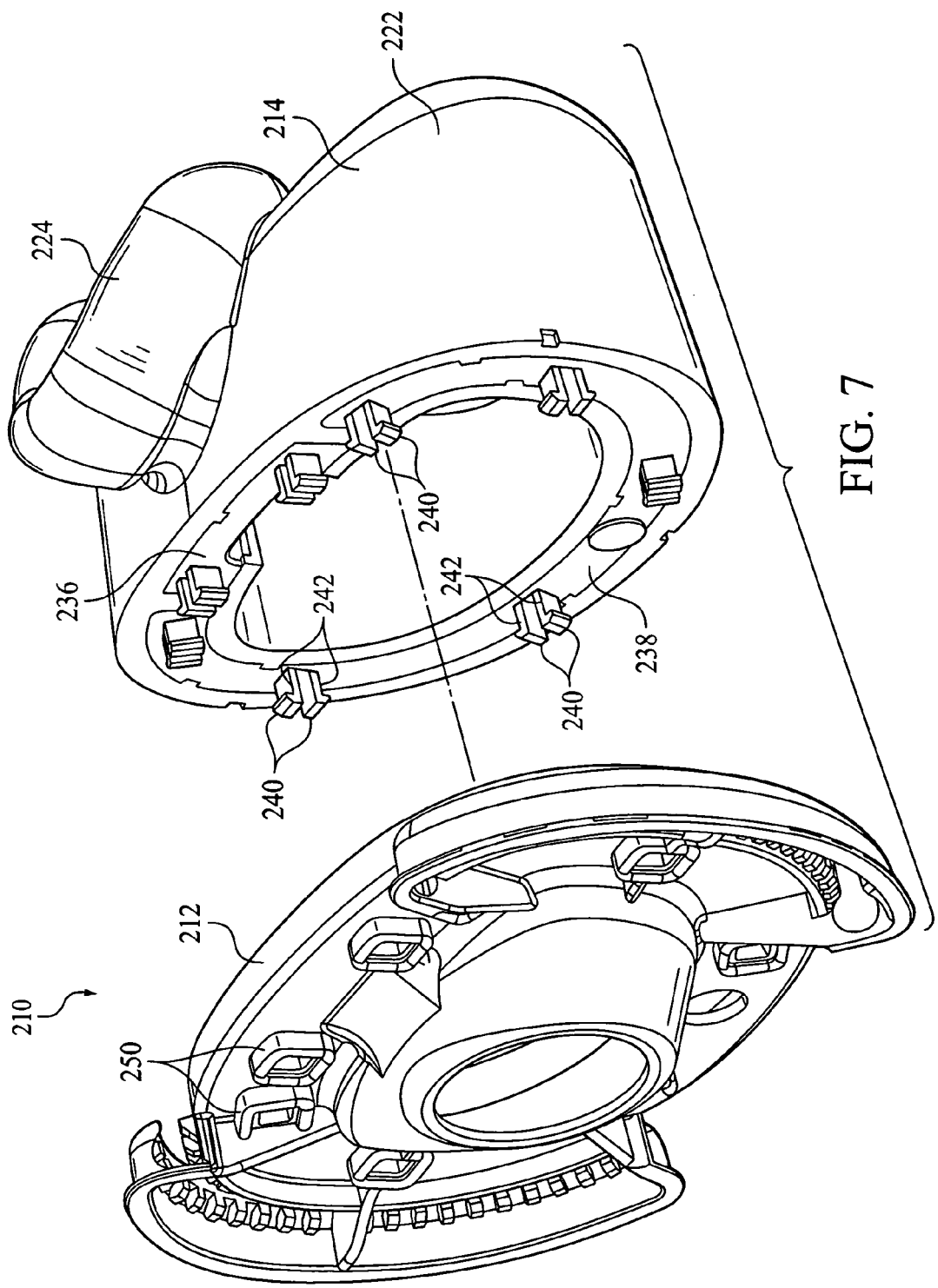
FIG. 7 is an exploded view of the patient interface of FIG. 6.
Figure 8:
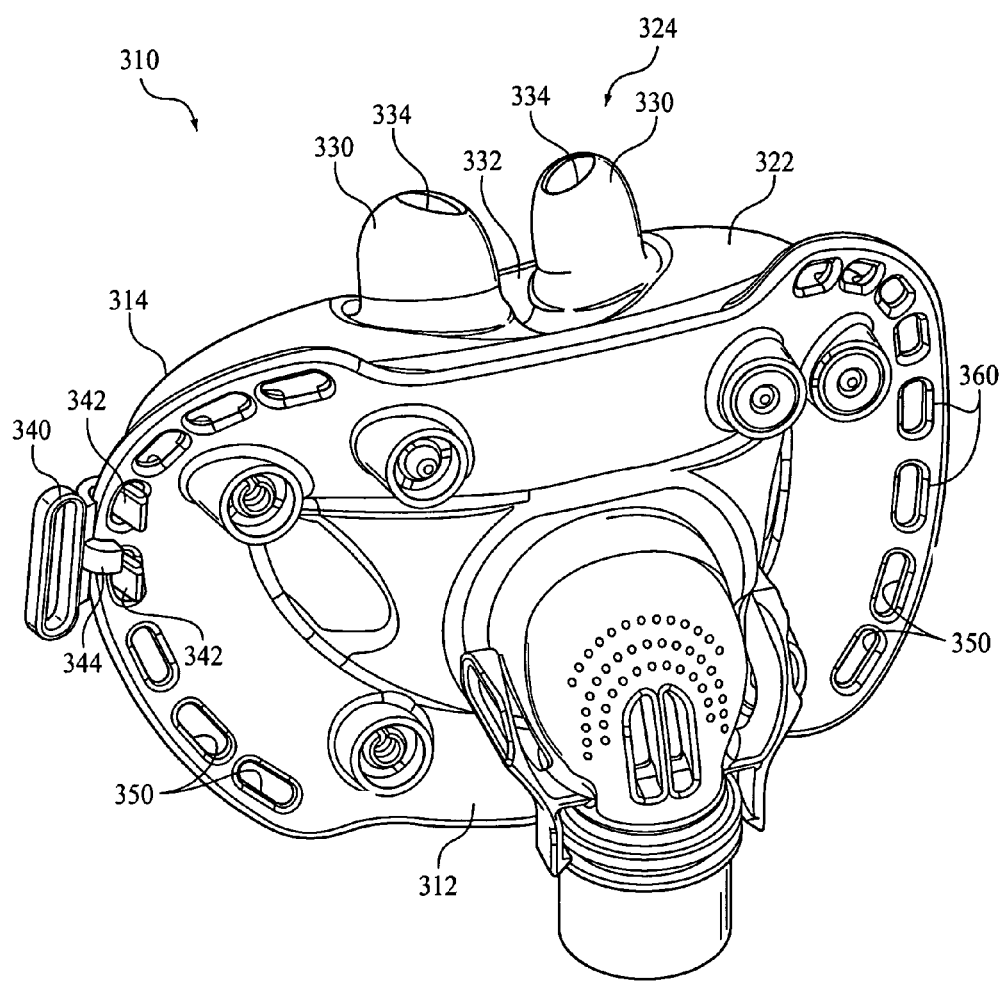
FIG. 8 is a front perspective view of a third embodiment of a patient interface according to the principles of the present invention.
Figure 9:
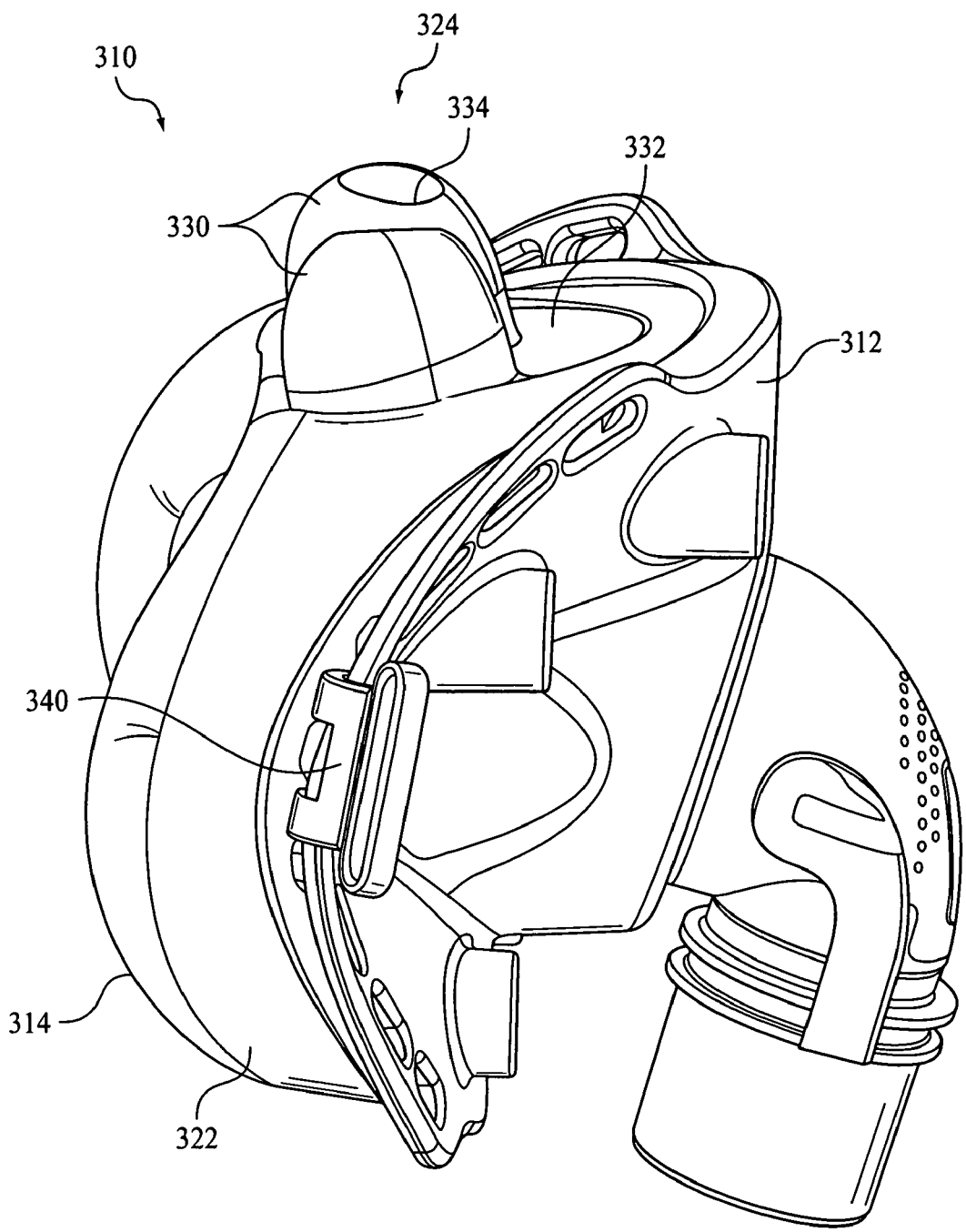
FIG. 9 is a side view of the patient interface of FIG. 8.
Figure 10:
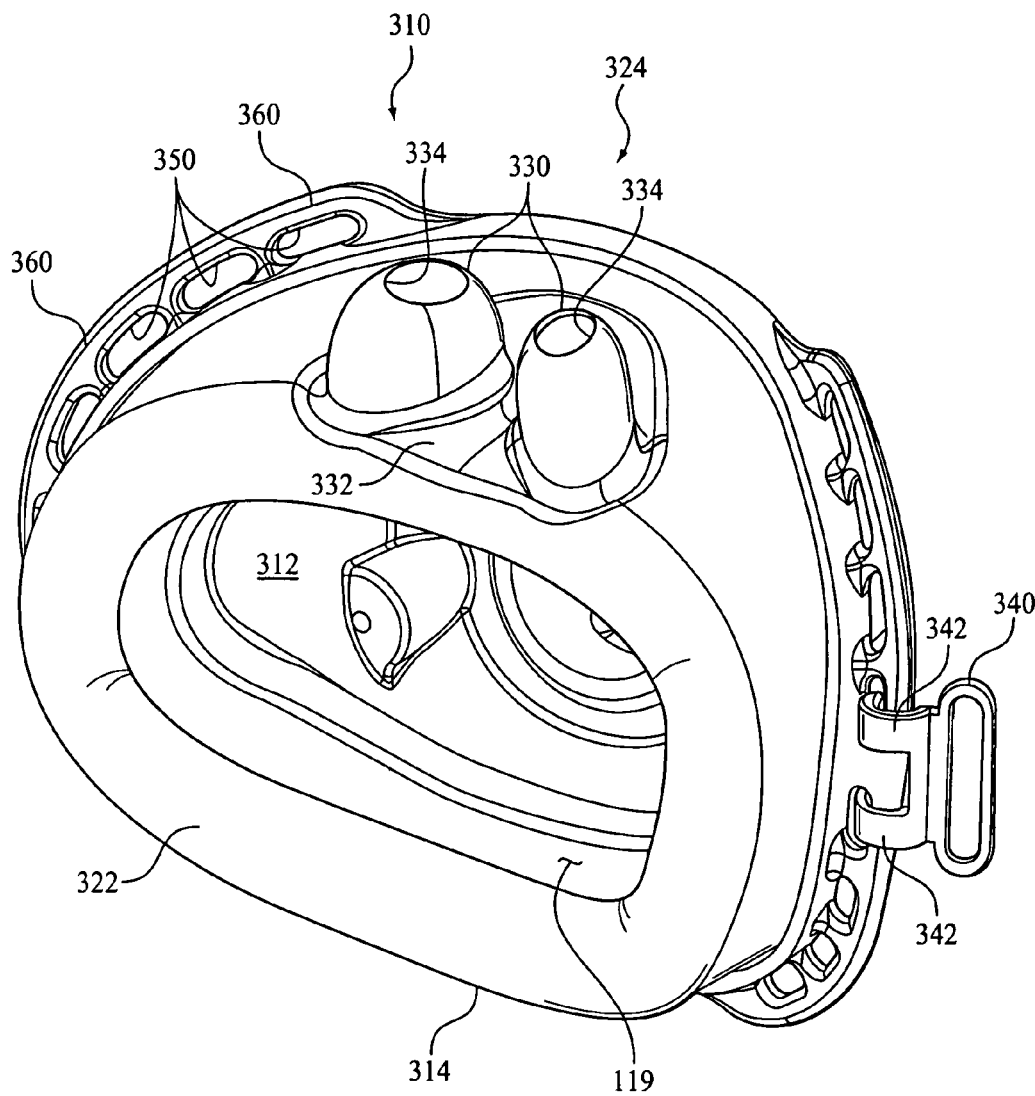
FIG. 10 is a rear perspective view of the patient interface of FIG. 8.
Figure 11:
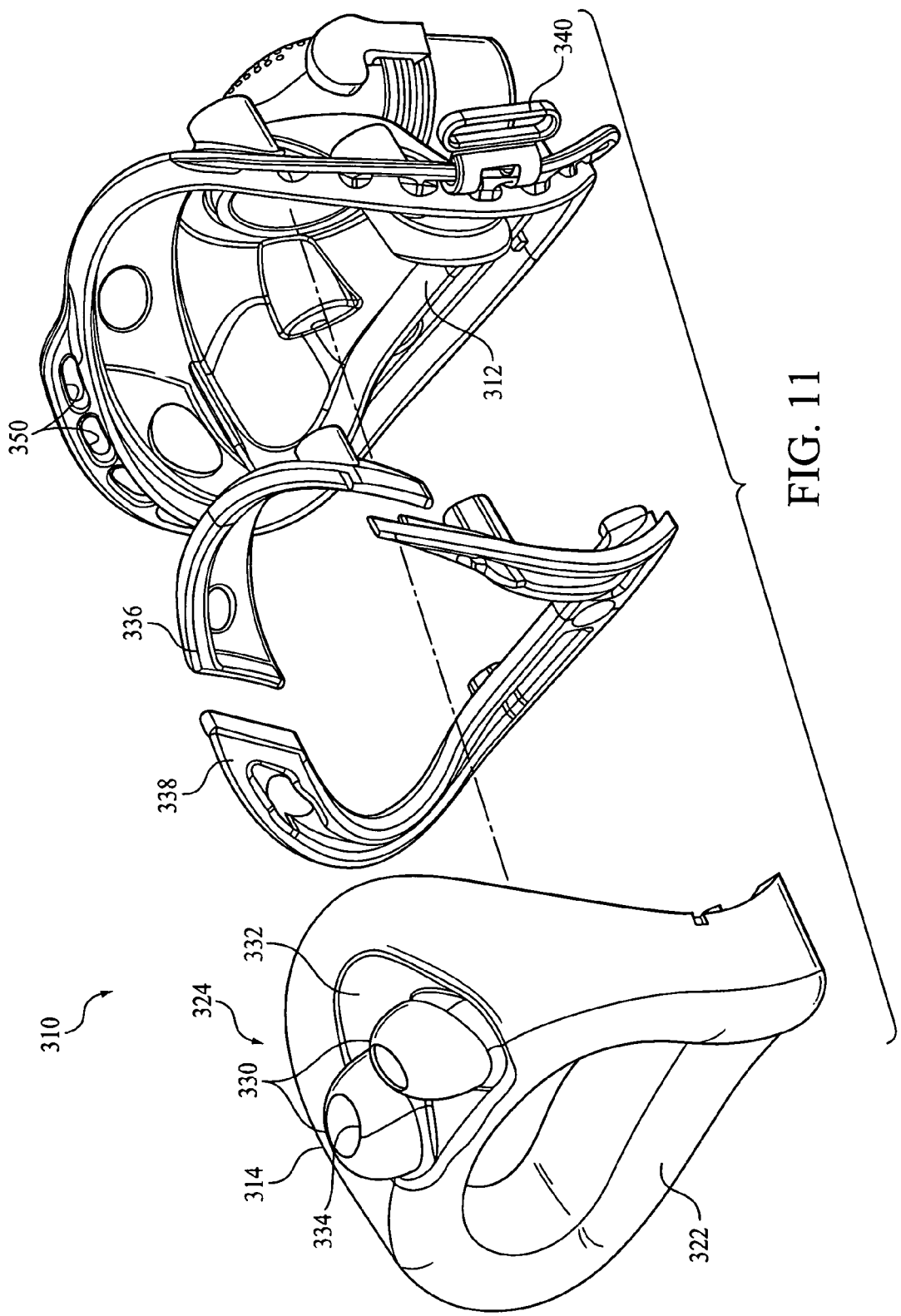
FIG. 11 is an exploded view of the patient interface of FIG. 8.
Figure 12:
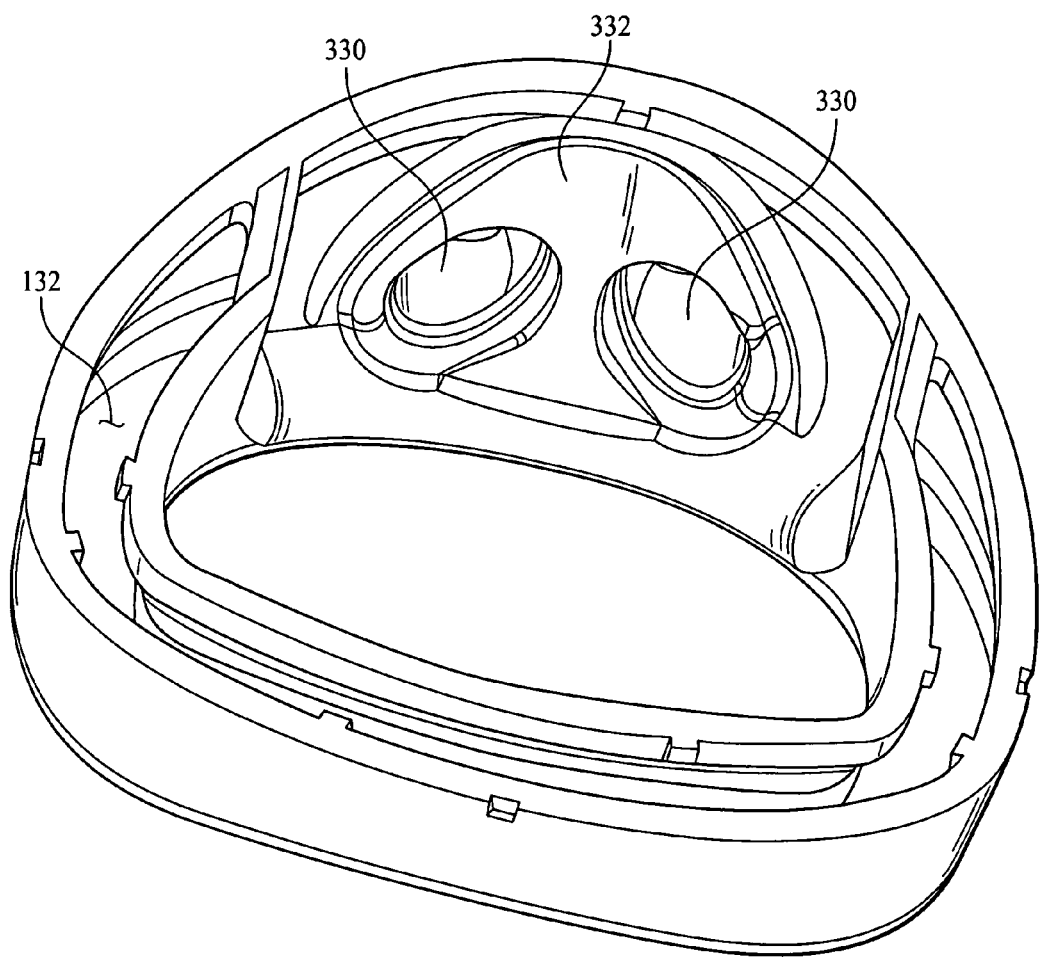
FIG. 12 is a rear perspective view of the seal member of the patient interface of FIG. 8.

A second exemplary embodiment is shown in FIGS. 6 and 7. In this embodiment, patient interface 210 includes a faceplate 212 and a seal member 214 having an oral cushion portion 222 and nasal interface portion 224. Faceplate 212, however, is not contoured as in the embodiment of FIGS. 1-5, but has a generally flat profile. A two-piece mounting ring defined by portions 236 and 238 are used to couple the seal member to the faceplate. Thus, portions 236 and 236 correspond to mounting rings 136 and 138 from the embodiment of FIGS. 1-6. Snapping members 240 in the form of dual snap members 240 on cantilever arms 242 are used to couple the portions of the mounting ring to the faceplate. Receptacles 250 are provided on faceplate 212 to receive these snap members.

It should be noted that while a two-piece mounting ring has been shown and described for mounting the seal member to the faceplate, rings defined by a single piece, or by more than two pieces, are contemplated by the present invention. In addition, the mounting ring can be made from any suitable material, such as plastic. It can be rigid, semi-rigid, or flexible. It can also be eliminated entirely if the seal member is mounted directly to the faceplate. As also noted above, other technique for fastening the mounting ring to the faceplate are contemplated by the present invention. For example, the present invention contemplates that the mounting ring surrounds the perimeter of the seal member and attached to the faceplate using tabs such that the seal member is captured between the mounting ring and the faceplate.

A third exemplary embodiment is shown in FIGS. 8-14. In this embodiment, patient interface 310 has a faceplate 312 and a seal member 314 having an oral cushion portion 322 and a nasal interface portion 324. However, the nasal interface portion in this embodiment is in the form of a nasal pillows or prongs 330 that are insertable into the nares of a user and structured to sealingly engage with nasal passages of a user's nose. Rather than wrapping or sealing against the exterior surface of the nose as in previous embodiments, nasal pillows 330 seal around each naris. Nasal interface portion 324 also includes a gusset or base portion 332 that supports nasal pillows 330. Each nasal pillow has a hole 334 in its distal end. Holes 374 communicate the user's airway with the pressurized interior 119 of patient interface 310. Like the embodiment of FIGS. 1-5, seal member 314 attaches to shell by a two-piece mounting ring 336, 338 (see FIG. 11).

Figure 13:
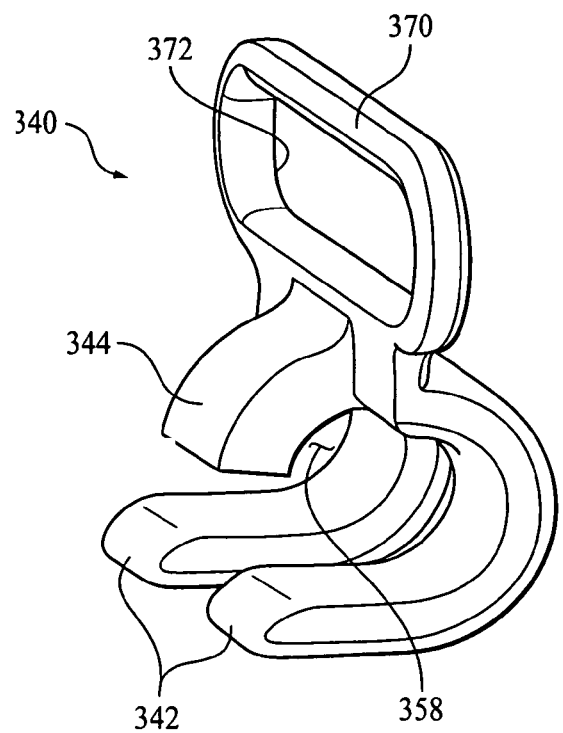
FIGS. 13 and 14 are front and rear perspective views of a headgear clip used in the patient interface of FIG. 8.
Figure 14:
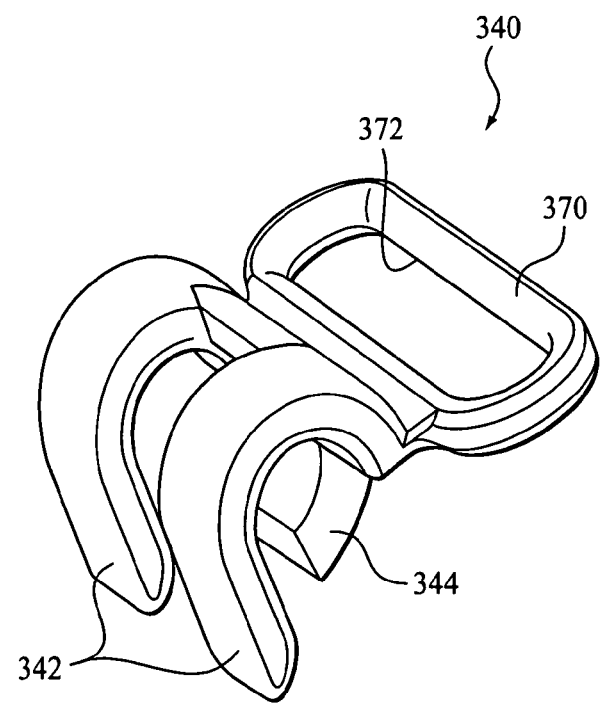

A headgear as shown, for example, in FIGS. 27-30, may be releasably attached to patient interface 310 by means of hook clips 340 that selectively attach to each side of faceplate 312. As shown in FIGS. 13 and 14, hook clips 340 include a pair of engaging arms 342 and a retaining arm 344. A number of openings 350 are provided on each side of faceplate 312 for receiving engaging arms 342 (see FIGS. 8 and 10). To position the engaging arms into openings 350 the user inserts the engaging arms in the openings and rotates hook clip 340 relative to the faceplate. Retaining arm 344 keeps the hook clip from falling off of the faceplate once the hook clip is properly attached to the faceplate. Engaging arms 342 and retaining arms 244 are configured, sized, and arranged such that a gap 358 is defined between the engaging arms and the retaining arm. Gap 358 is large enough to accommodate a portion 360 of a rail provided on the edge of the faceplate.

Hook clip 340 includes a headgear strap retaining portion 370 where the headgear strap attaches to the hook clip. In the illustrated embodiment, the strap retaining portion includes a slot 372. The headgear strap (not shown) inserts through slip 372 for attaching the strap to hook clip 340. It is to be understood that the present invention contemplates that the headgear strap can be attached to hook clip 340 using any technique, such as snap, hook, or other fastening mechanism.

Figure 15:
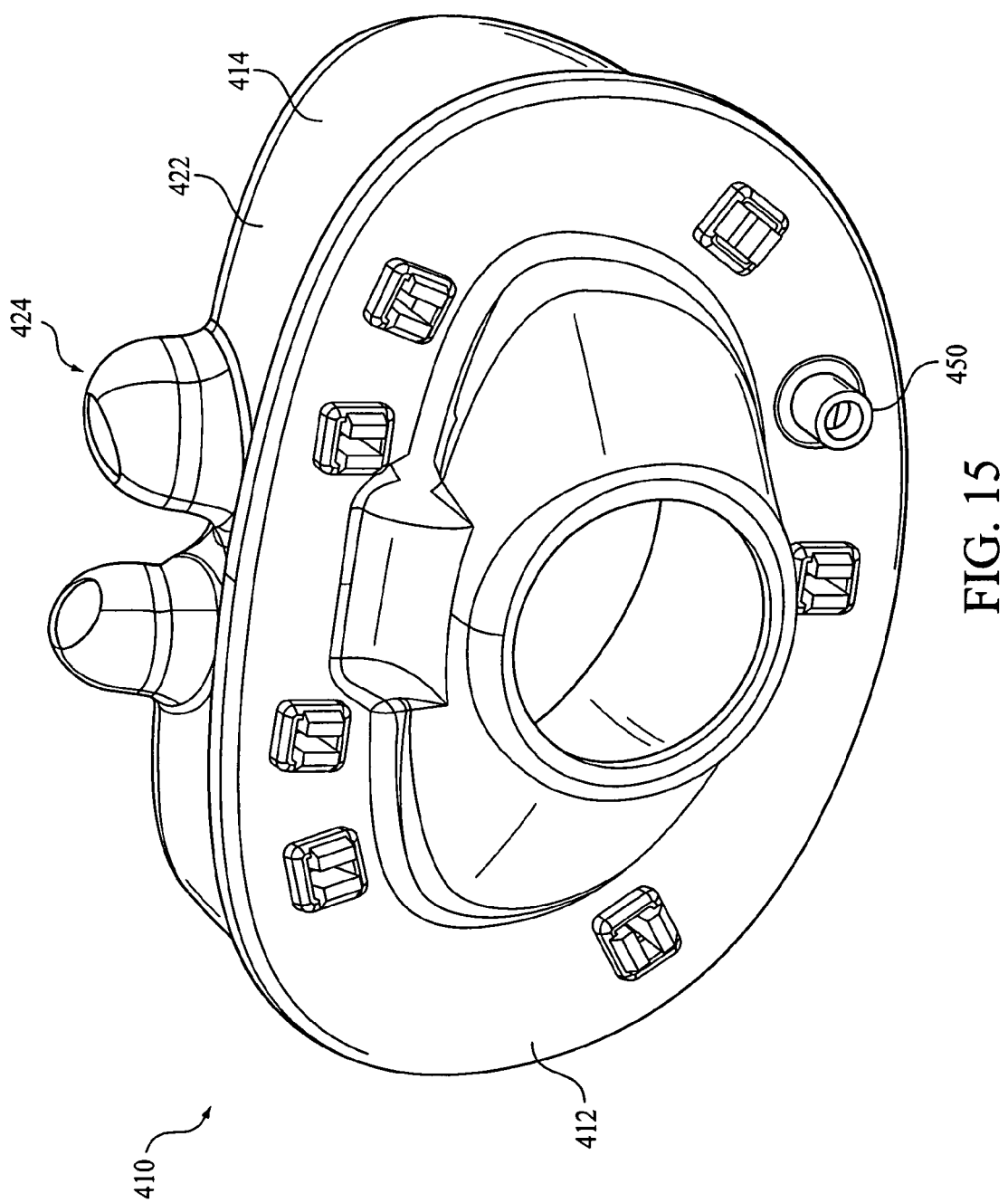
FIG. 15 is front perspective view of a fourth embodiment of a patient interface according to the principles of the present invention.
Figure 16:
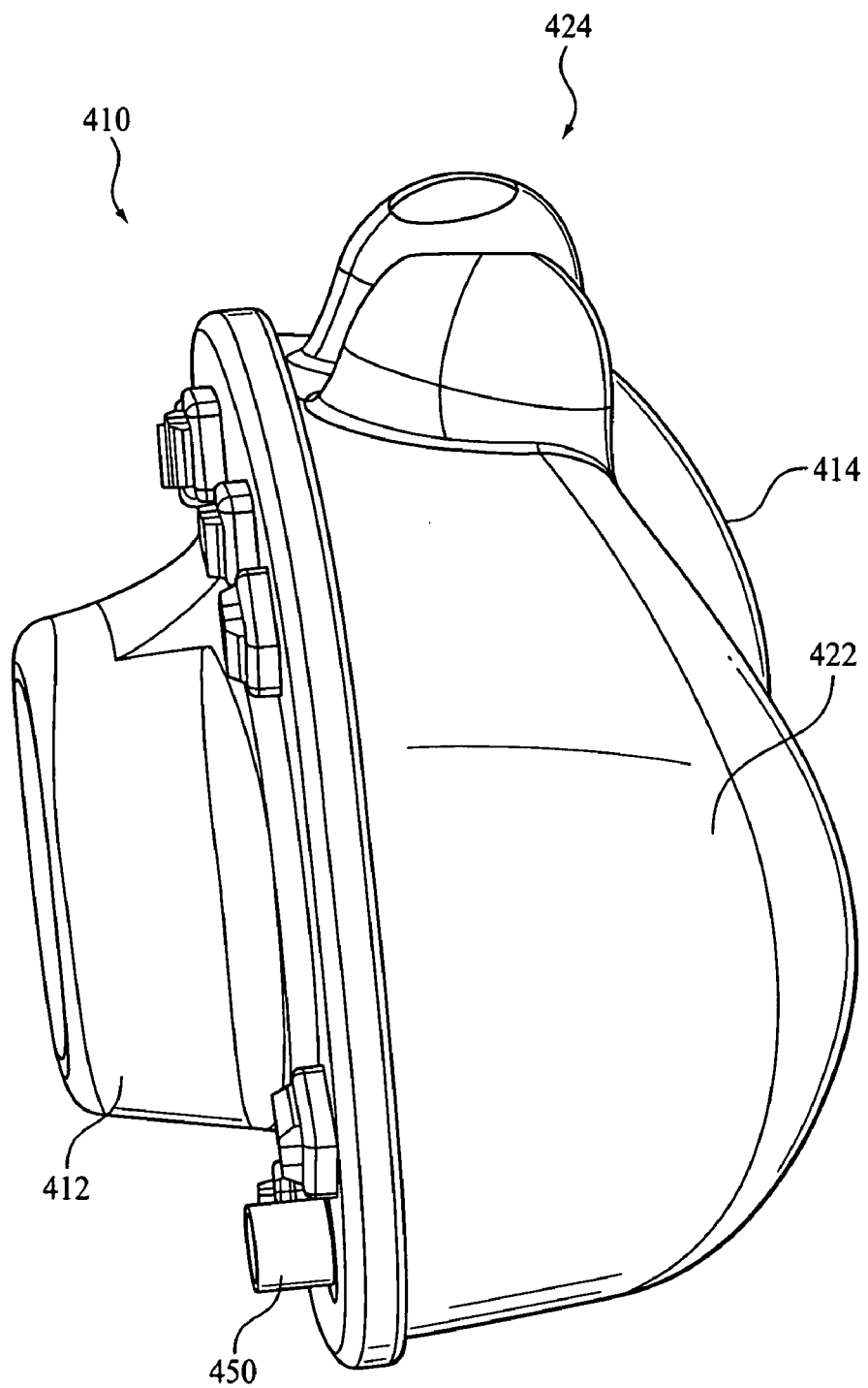
FIG. 16 is a side view of the patient interface of FIG. 15.
Figure 17:
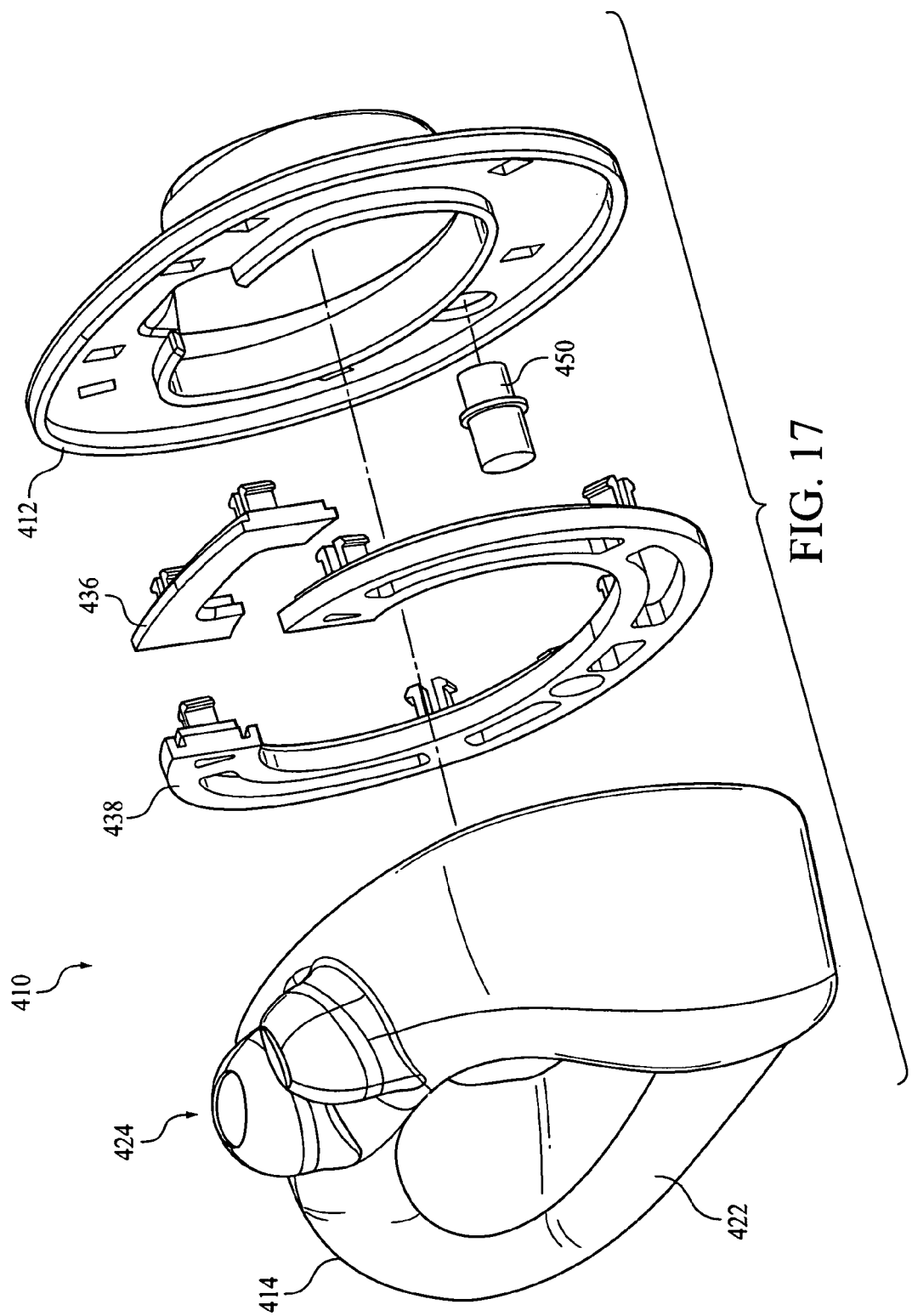
FIG. 17 is an exploded view of the patient interface of FIG. 15.
Figure 18:
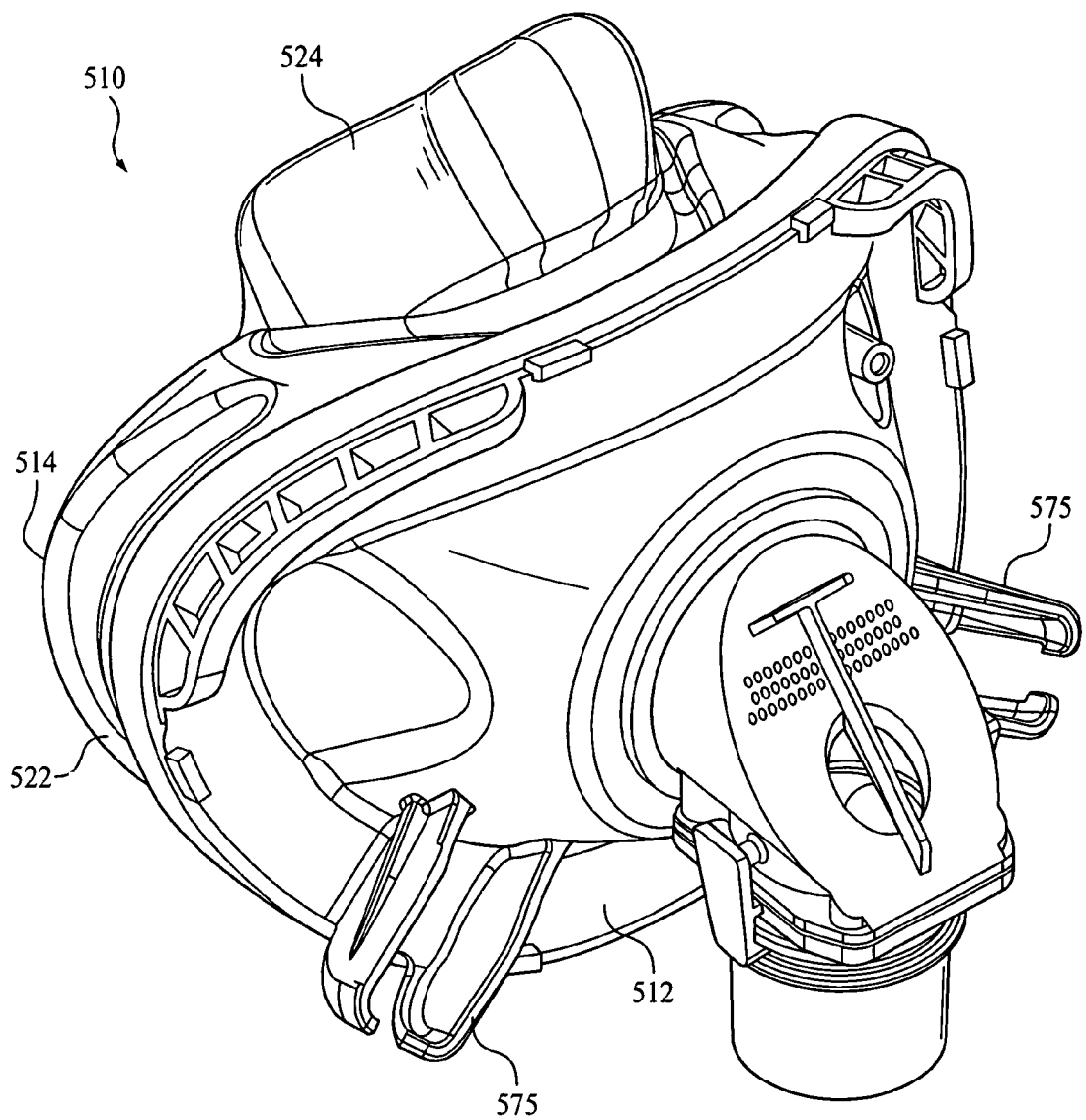
FIG. 18 is front perspective view of fifth embodiment of a patient interface according to the principles of the present invention.
Figure 19:
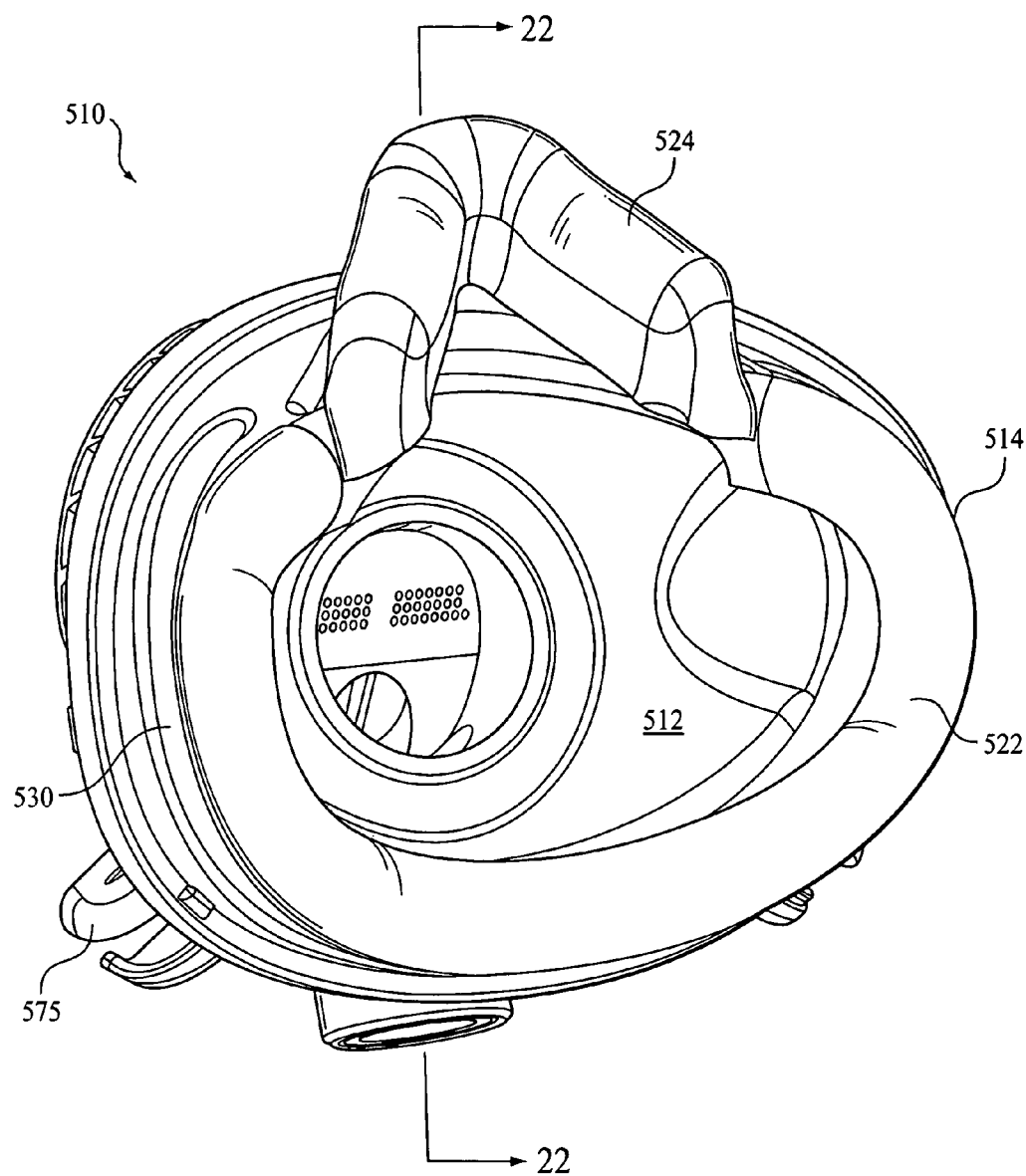
FIG. 19 is a rear perspective view of the patient interface of FIG. 18.
Figure 20:
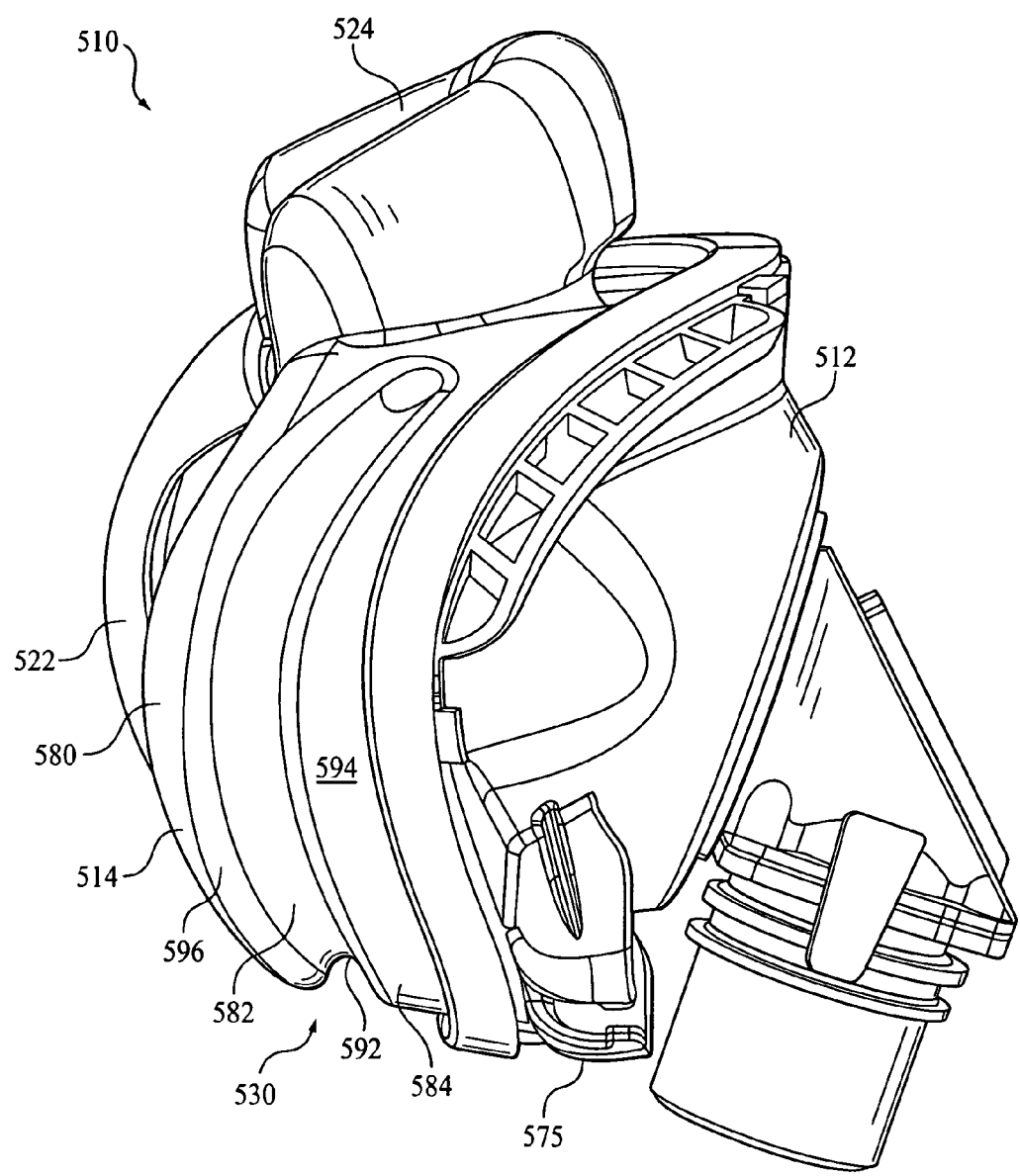
FIG. 20 is a side view of the patient interface of FIG. 18.
Figure 21:
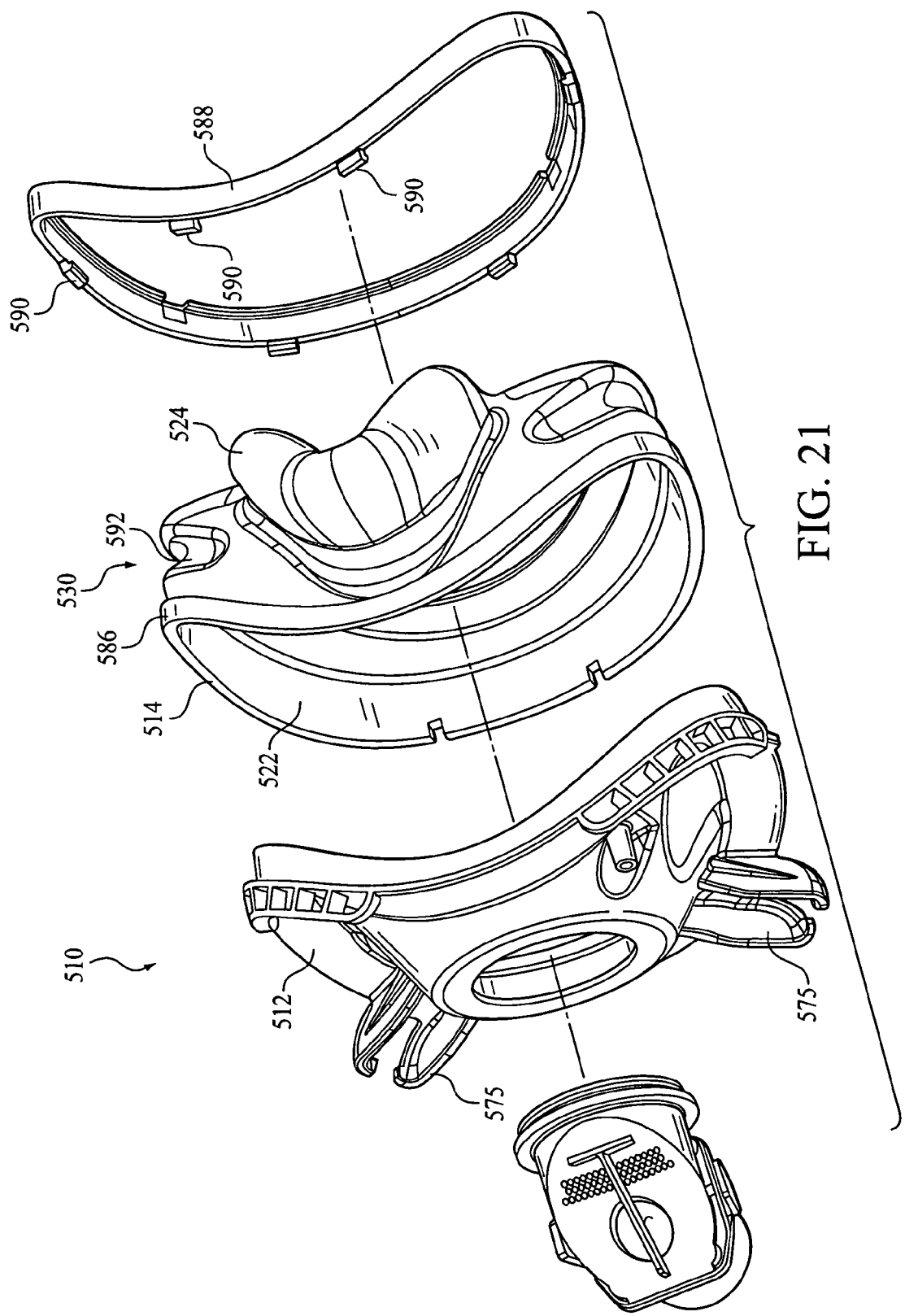
FIG. 21 is an exploded view of the patient interface of FIG. 18.
Figure 22:
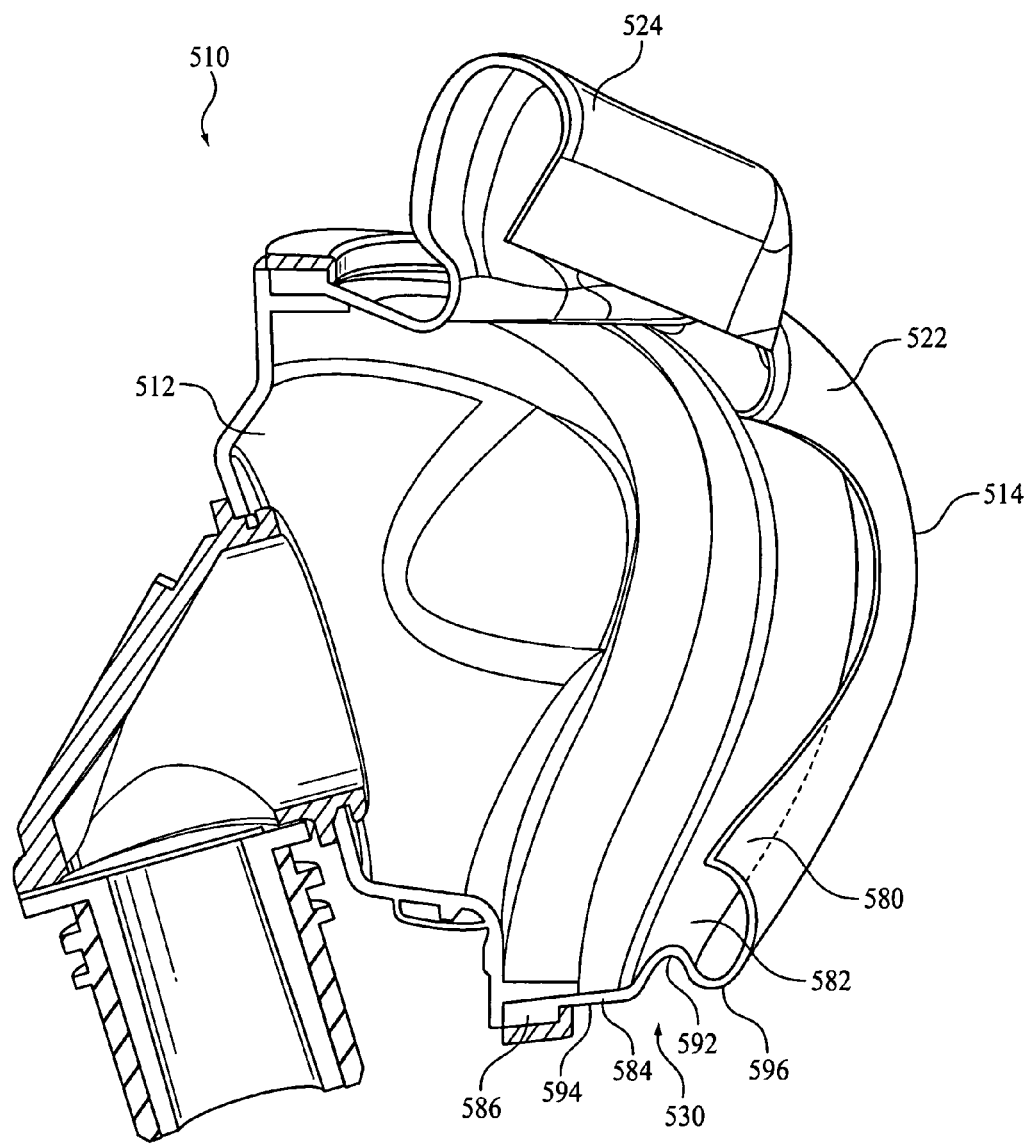
FIG. 22 is a cross-sectional view of the patient interface of FIG. 18 taken along line 22-22 of FIG. 19.

A fourth exemplary embodiment is shown in FIGS. 15-17. In this embodiment, patient interface 410 includes a faceplate 412 and a seal member 414 having an oral cushion portion 422 and nares interface portion 424. Faceplate 412, however, is not contoured, as in the embodiment of FIGS. 8-14, but has a flat profile, like the faceplate shown in the embodiment of FIGS. 6 and 7. Seal member 414 attaches to shell 412 by means of a two-piece mounting ring 436, 438. A valve 450 as discussed above, is provided for selectively inflating and deflating oral cushion portion 422 of seal member 414.

A fifth exemplary embodiment is shown in FIGS. 18-22. In this embodiment, patient interface 510 includes a faceplate 512 and a seal member 514 having an oral cushion portion 522 and nasal interface portion 524. In this embodiment, oral cushion portion 522 is a single wall cushion having a pleat 530 defined in at least a portion of the wall. As in the previous embodiment of FIGS. 1-5, nasal interface portion 524 in the form of a cup-shaped protrusion integral with and extending from oral cushion portion 522. Oral cushion portion 522 is configured to surround the mouth of the user and side wall that includes a flap portion 580, a middle portion 582 and a base portion 584.

Flap portion 580 is configured to provide a secure seal between the oral cushion portion and the surface of the user. Base portion 584 includes an annular collar 586 of increased thickness, which may be captured between shell and a retaining ring 588 having spaced capture members 590 to form a seal with the faceplate. Middle portion 582 includes a pleat 530 on the sides and bottom portion thereof. Pleat 530 provides an integral corrugation, which provides a spring-type action. Pleat 530 is in the form of a groove that wraps around the sides and bottom of the oral cushion portion 522. The single wall of oral cushion portion 522 with a pleat 530 of the present invention imitates the floating effect of double flap cushions, such as those disclosed in U.S. Pat. No. 4,971,451, the disclosure of which is incorporated herein by reference.

A sidewall portion 594 of the oral cushion portion between annular collar 586 and groove 592 is substantially thicker than a sidewall portion 596 between pleat 530 and flap portion 580 to provide support. Groove 592 also varies in depth, having a deeper profile at the cheek area. A patient interface having a cushion with a pleat is disclosed in U.S. provisional patent application Ser. No. 11/312,026 (publication no. US-2006-0130844-A1) ("the '026 application"), the disclosure of which is incorporated by reference herein. One of ordinary skill in the can appreciate the seal member may take other forms, such as a cushion without a pleat or with multiple pleats provided at various locations around the seal member.

A headgear, such as those illustrated in FIGS. 27-30 may be releasably attached to patient interface 510 by through a ball-and-socket connection. In the illustrated embodiment, the lower corners of faceplate 512 include headgear attaching elements in the form of socket attachment elements 575 that cooperate with corresponding ball elements (not illustrated) on headgear straps. The ball-and-socket configuration, and examples of other headgear attachment configurations suitable for use with the present invention, are disclosed in the '179 patent.

Figure 23:
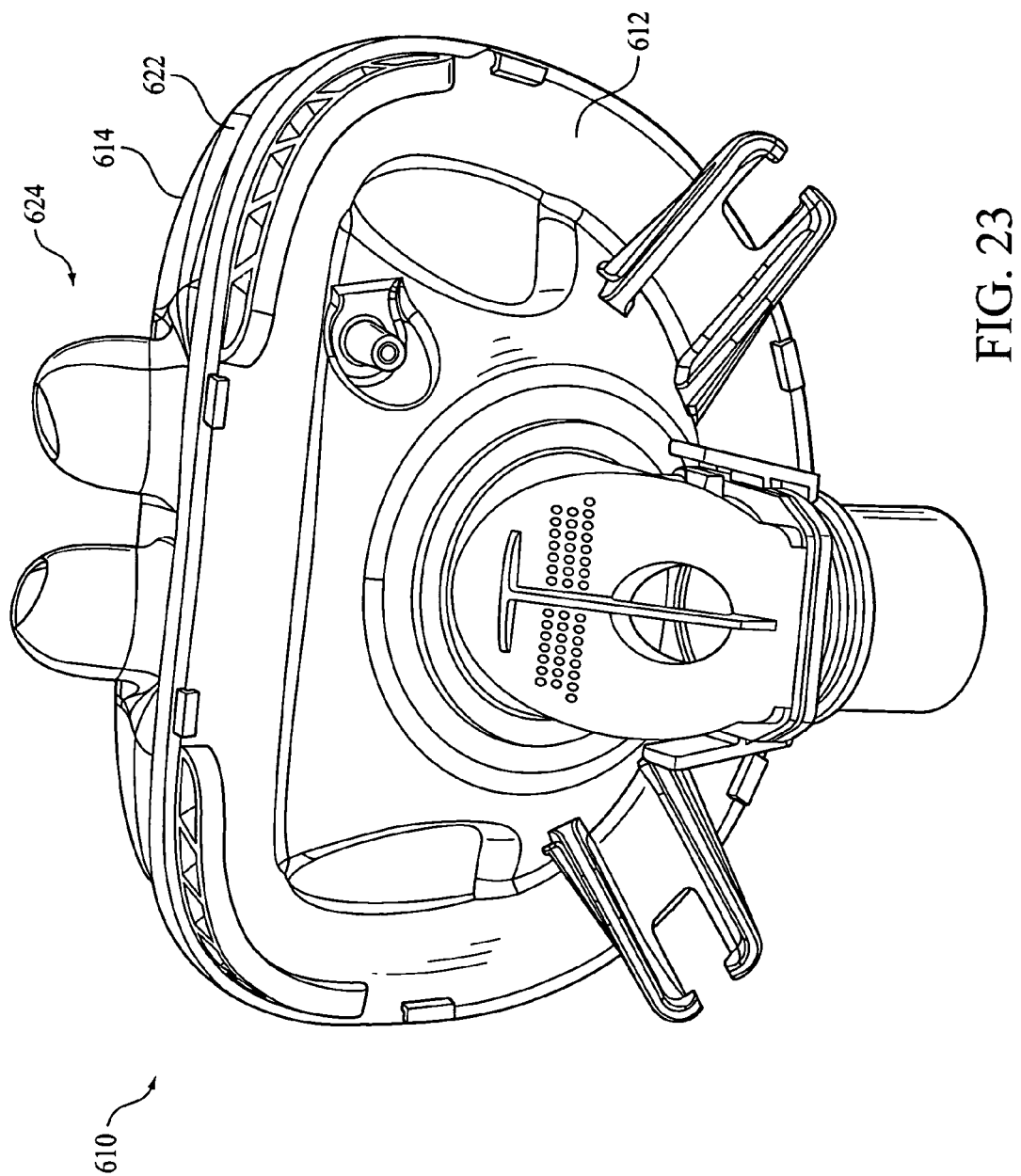
FIG. 23 is front perspective view of a sixth embodiment of a patient interface according to the principles of the present invention.
Figure 24:
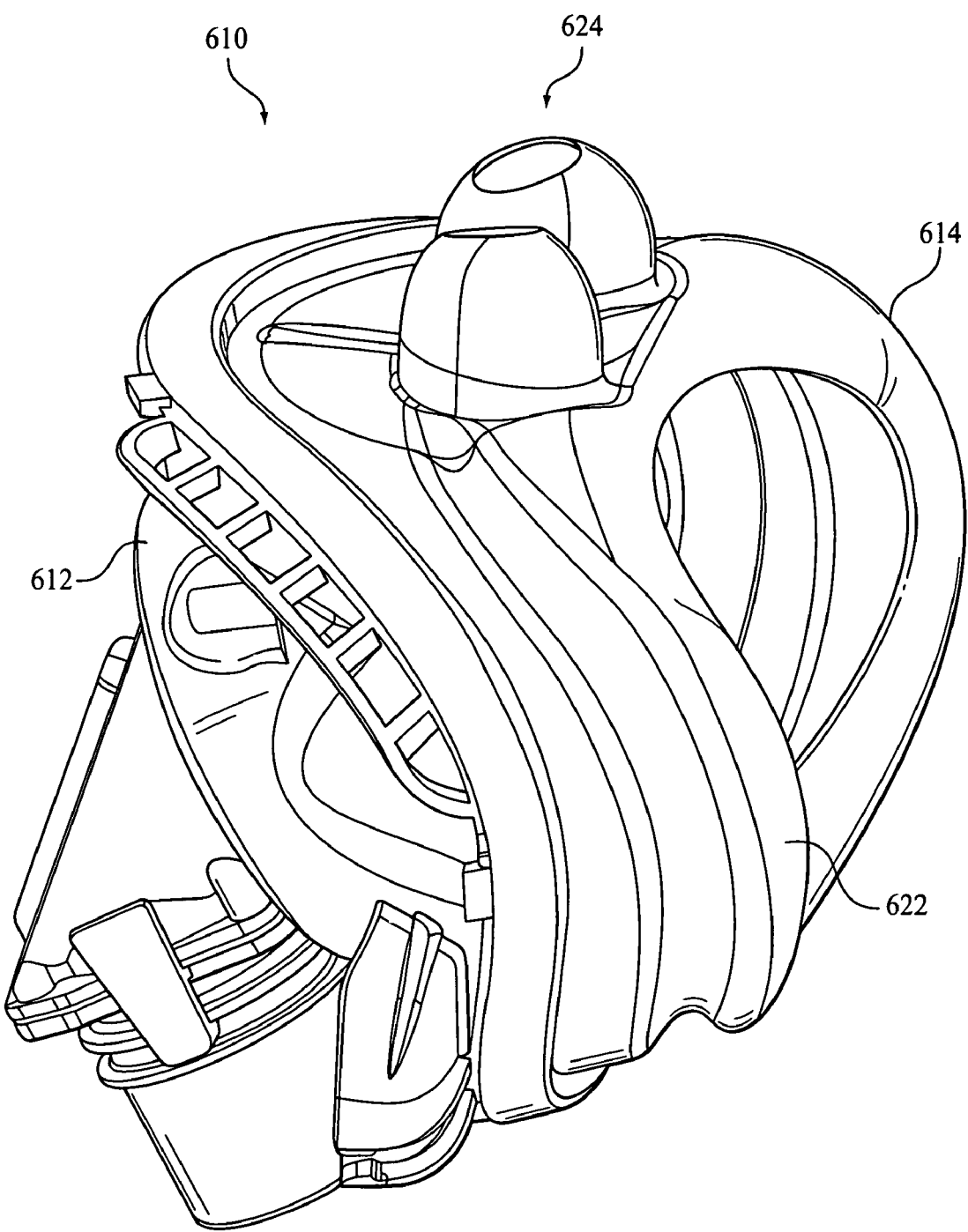
FIG. 24 is a side view of the patient interface of FIG. 23.

A sixth exemplary embodiment is shown in FIGS. 23 and 24. In this embodiment, patient interface 610 includes a faceplate 612 and a seal member 614 having an oral cushion portion 622 and nasal interface portion 624. Patient interface 610 includes a combination of features from previous embodiments. More specifically, seal member 614 has an oral cushion portion 622 having a pleat 630, such as that shown in FIGS. 18-22, and a nasal interface portion 624, such as that shown in FIGS. 8-14.

Figure 25:
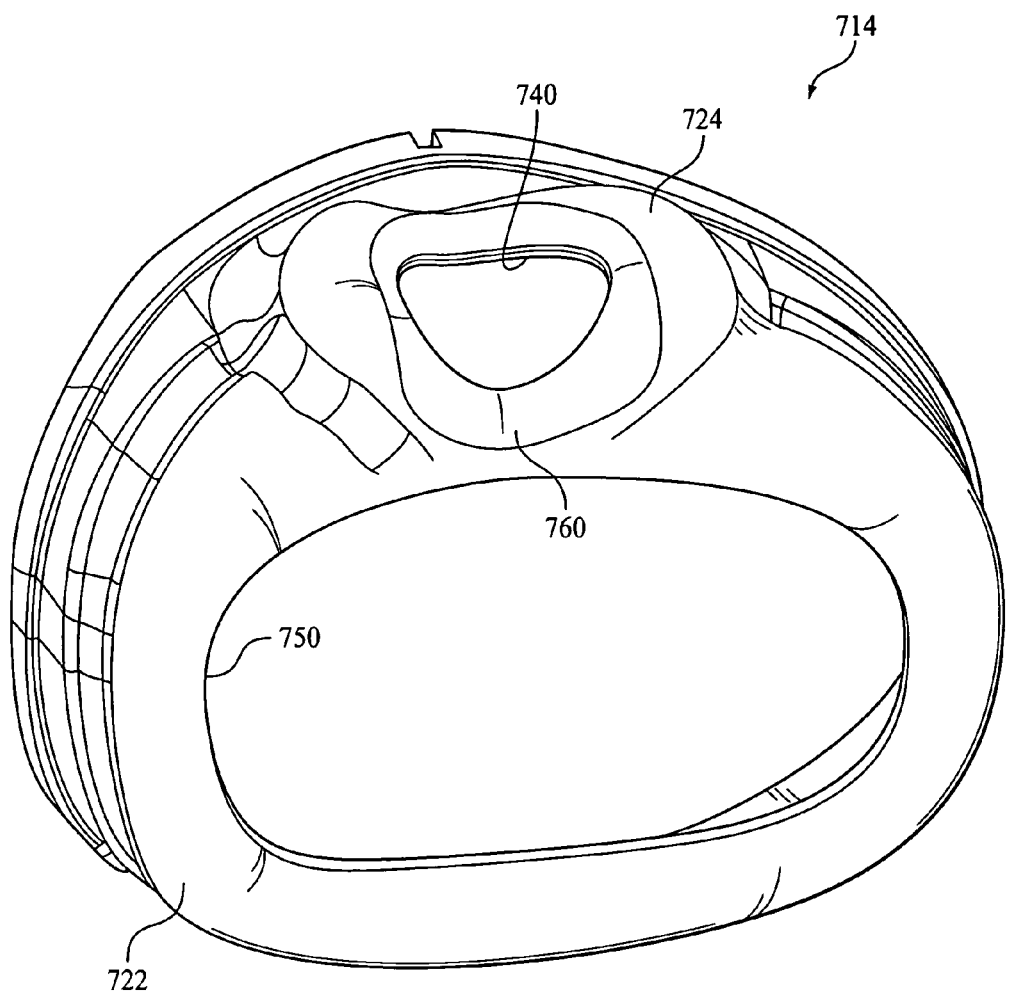
FIG. 25 is a first rear perspective view of a seventh embodiment for a seal member according to the principles of the present invention.
Figure 26:
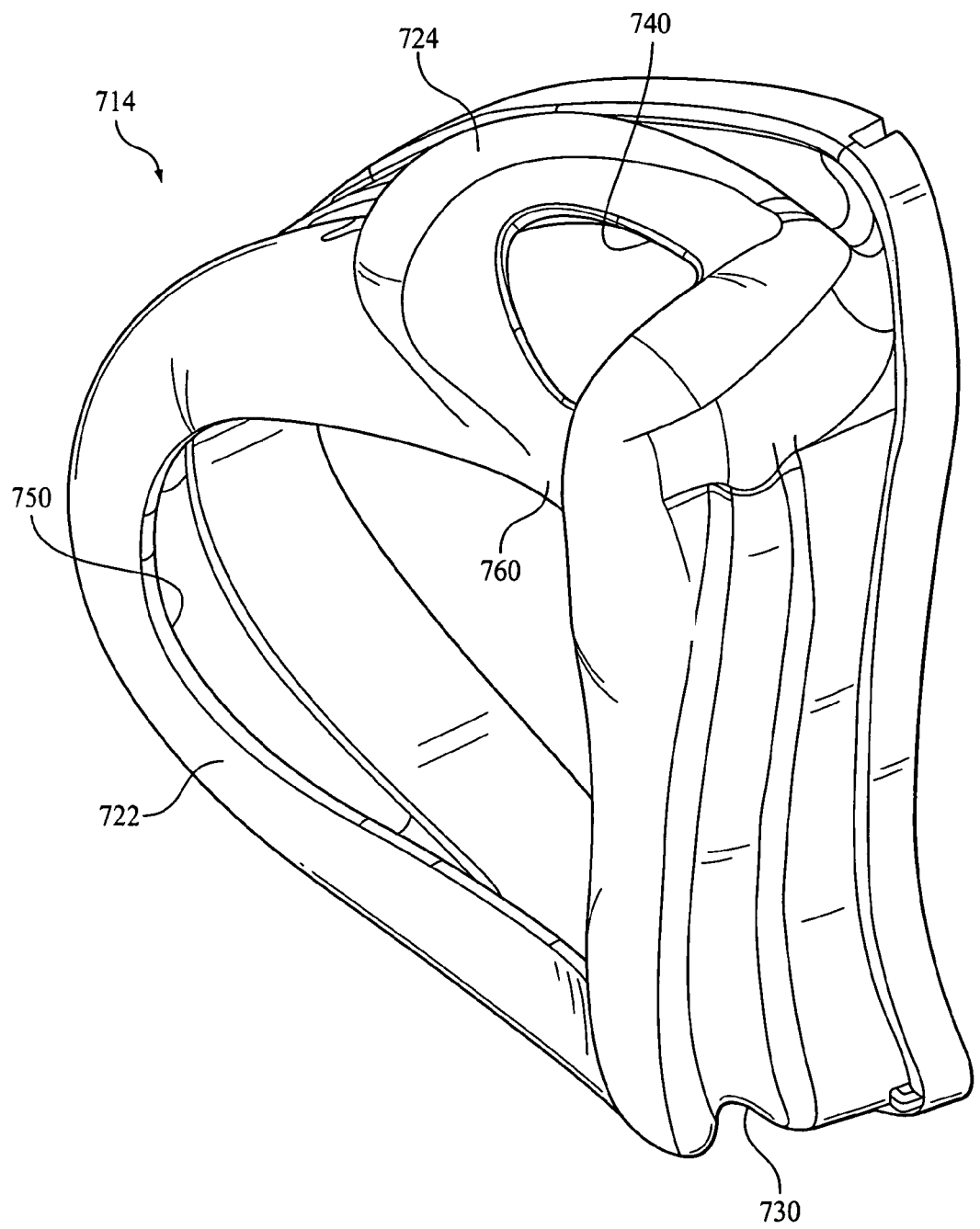
FIG. 26 is a second rear perspective view of the seal member of FIG. 25.

FIGS. 25 and 26 illustrate a further embodiment for a seal member 714 suitable for use in the patient interface of the present invention. In this embodiment, seal member includes an oral cushion portion 722 and a nasal interface portion 724. Oral cushion portion 722 is a single wall cushion having a pleat 730 defined in at least a portion of the sidewall. In the illustrated embodiment, the pleat extends around the entire perimeter of the oral cushion portion and terminates at each side of the nasal interface portion. Nasal interface portion 724 is defined by a cup-shaped protrusion integral with and extending from oral cushion portion 722. Nasal interface portion includes a first opening 740 and oral cushion portion 722 includes a second opening 750. A web of material 760 separates first opening 740 from second opening 750. However, both openings 740 and 750 communicate with the interior chamber defined by the patient interface. It can be appreciated that in this embodiment, the nasal interface portion has a relatively low profile, meaning that it does not protrude very far from the oral cushion portion of the seal member.

FIGS. 27-30 illustrate various embodiments for the patient interfaces according to the principles of the present invention, shown worn by a user as part of various patient interface assemblies. It is to be understood that these figures illustrate only a few exemplary configurations for the patient interface assembly and is not intended to be an exhaustive illustration of all possible embodiments.

Figure 27:
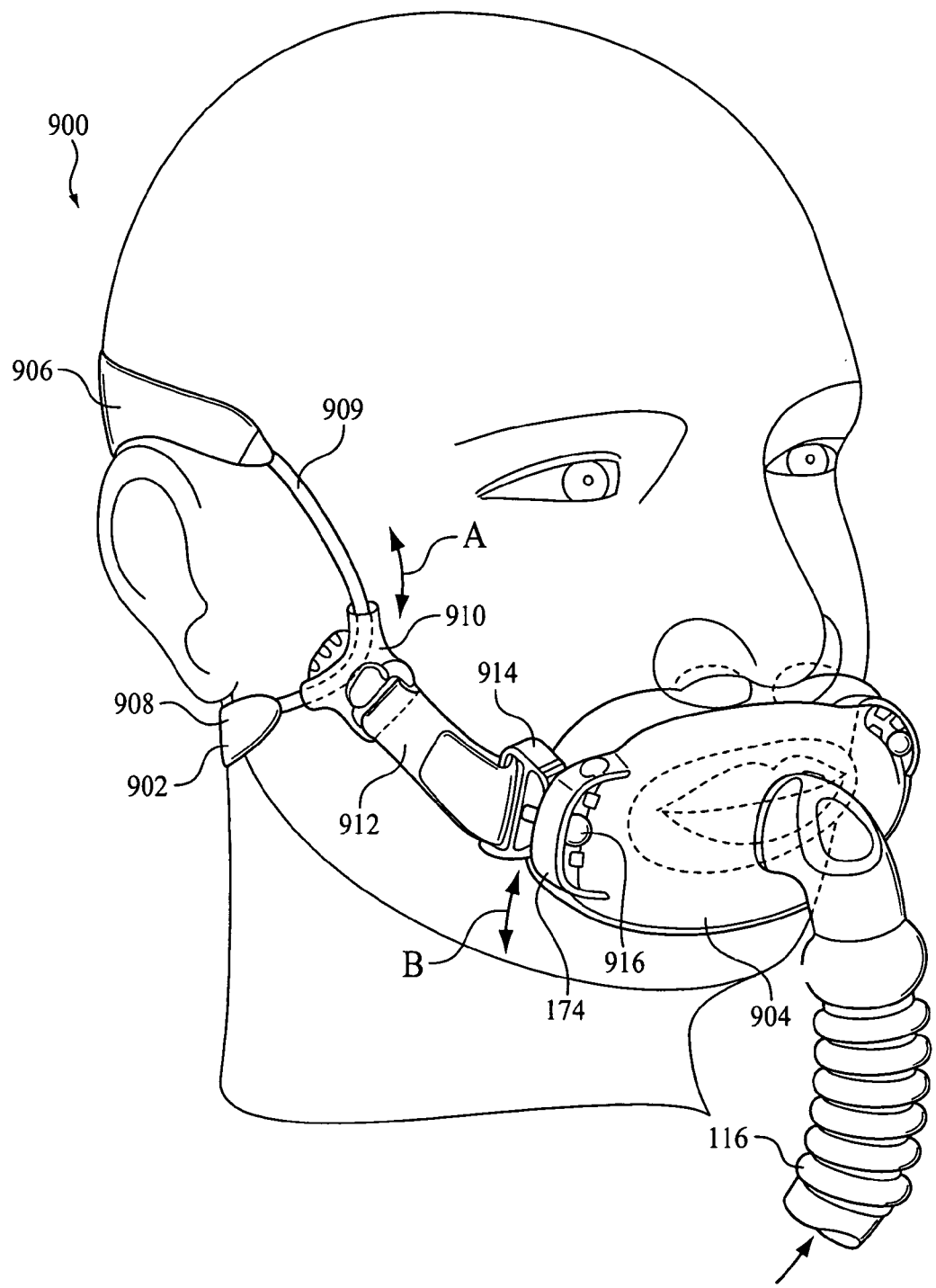
FIGS. 27-30 are perspective views of eighth-eleventh embodiments for the patient interfaces according to the principles of the present invention shown being worn by a user as part of various patient interface assemblies.

FIG. 27 illustrates an eighth embodiment of patient interface assembly 900 that includes a headgear 902 and a patient interface 904. Patient interface 904 corresponds to patient interface 110 except that the nasal interface portion includes a pair of nasal pillows rather than a cup-shaped cushion. Headgear 902 includes a pair of straps 906 and 908 that extend around the back of the user's head and are joined together at strip portion 909. A coupling member 910 is coupled to strip portion 909 such that the coupling member is selectively moveable along the strip portion as indicated by arrow A. The position of coupling member 910 on strip portion 909 can be controlled by a locking mechanism (not shown) or it can be left uncontrolled, so that the coupling member seeks the optimum position on the strip portion for each user. A connecting strap 912 connects coupling member 910 to a headgear clip 914.

Headgear clip 914 corresponds to the headgear clip shown in the '133 application and includes a portion 916 that is selectively positionable along rail 174. Headgear clip 914 also corresponds to the headgear clips disclosed in the '179 patent, and the '932 patent, and the '111 application. In this manner, the connection between the headgear and the patient interface can be adjusted, as indicated by arrow B, to suit the particular needs/desires of the user. As can be appreciated from this figure, the entire body of the patient interface remains below the bridge of the nose. The lower most portion of the bridge of the nose is indicated by a reference numeral 920. The patient interface of the present invention does not go any further up the nose toward the eye than this point.

Figure 28:
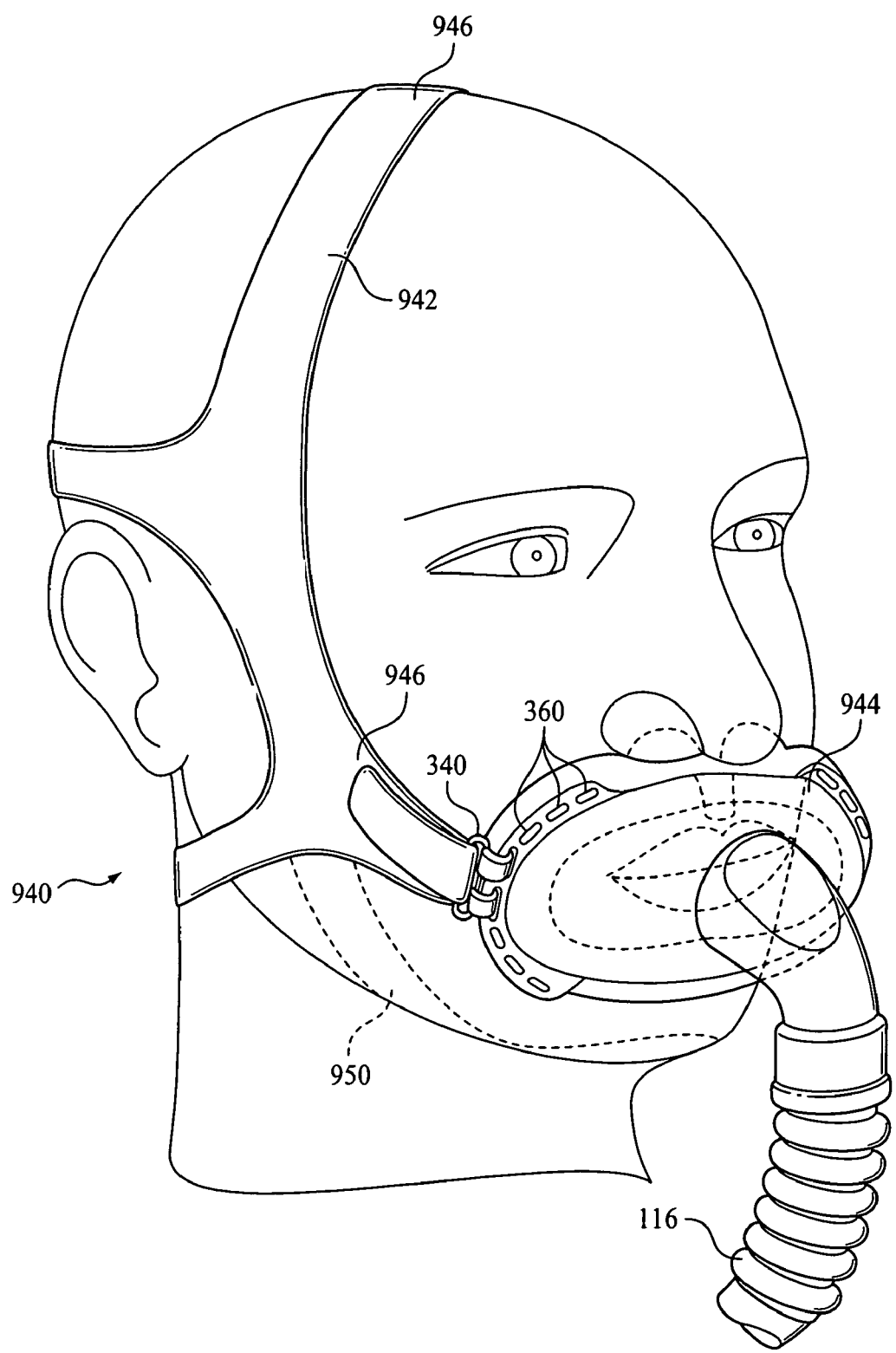

FIG. 28 illustrates a ninth embodiment of a patient interface assembly 940 that includes a headgear 942 and a patient interface 944. Patient interface 944 corresponds to patient interface 310. In this embodiment, headgear straps 946 are coupled to the faceplate of the patient interface using a hook clip 340, as discussed above with respect to the embodiment illustrated in FIGS. 8-14. Hook clip 340 can be located in any pair of openings 360 to suit the particular needs/desires of the user. In addition to straps that wrap around the back of the head, headgear 942 includes a strap 948 that wraps over the top of the head. An optional chin strap is shown by dashed lines 950. The present invention also contemplates providing a cap in addition to, or in place of the headgear straps. An example of such a cap is disclosed in U.S. Pat. No. 6,805,117.

Figure 29:
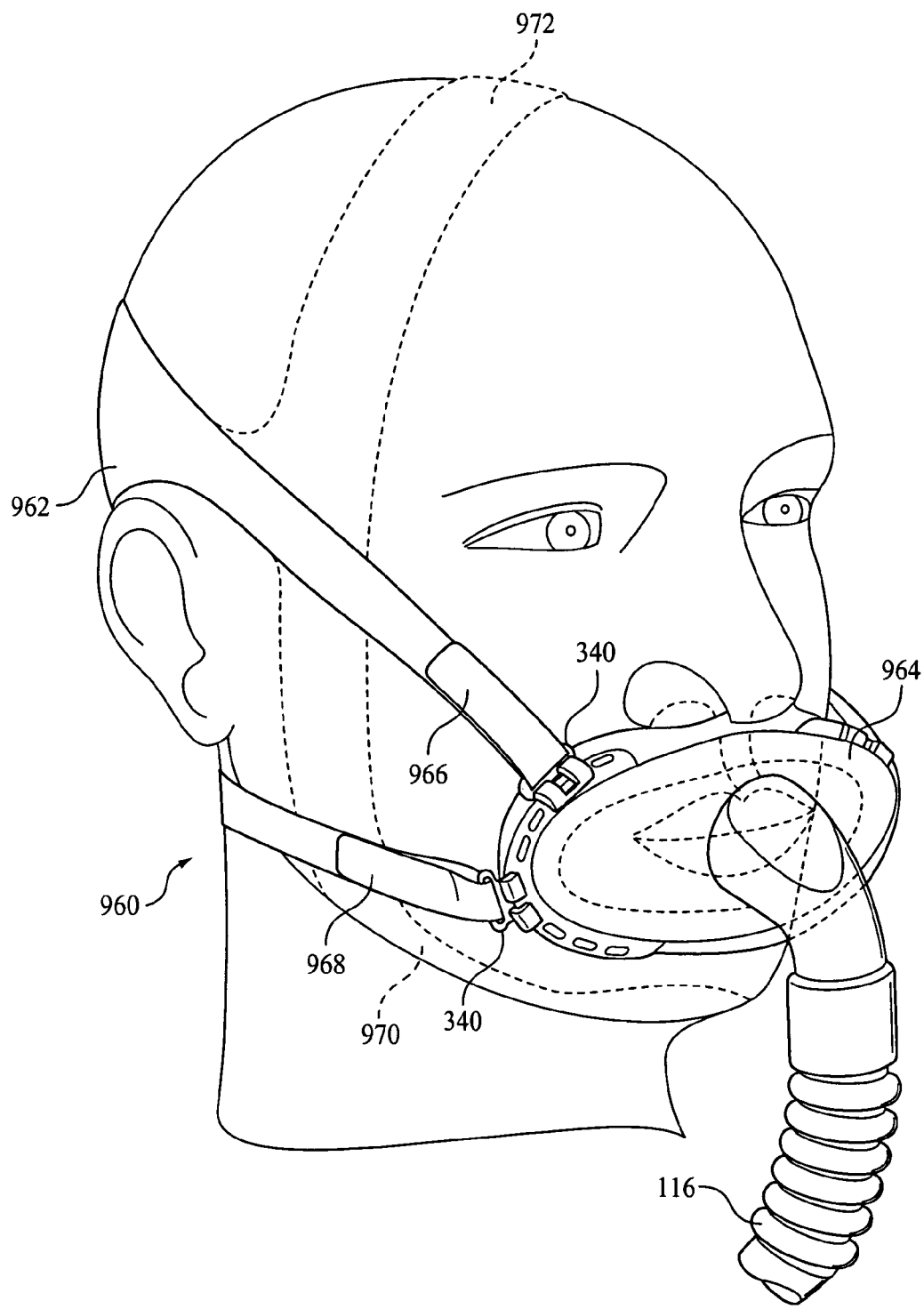

FIG. 29 illustrates a tenth embodiment of a patient interface assembly 960 that includes a headgear 962 and a patient interface 964. Patient interface 964 corresponds to patient interface 310. In this embodiment, headgear 962 includes two attachment points with the faceplate of patient interface 964. In other words, two hook clips 340 are disposed on one side of the faceplate to connect a first strap 966 and a second strap 968 to the faceplate. An optional chin strap is shown by dashed lines 970, and an optional over the head strap is shown by dashed lines 972.

Figure 30:
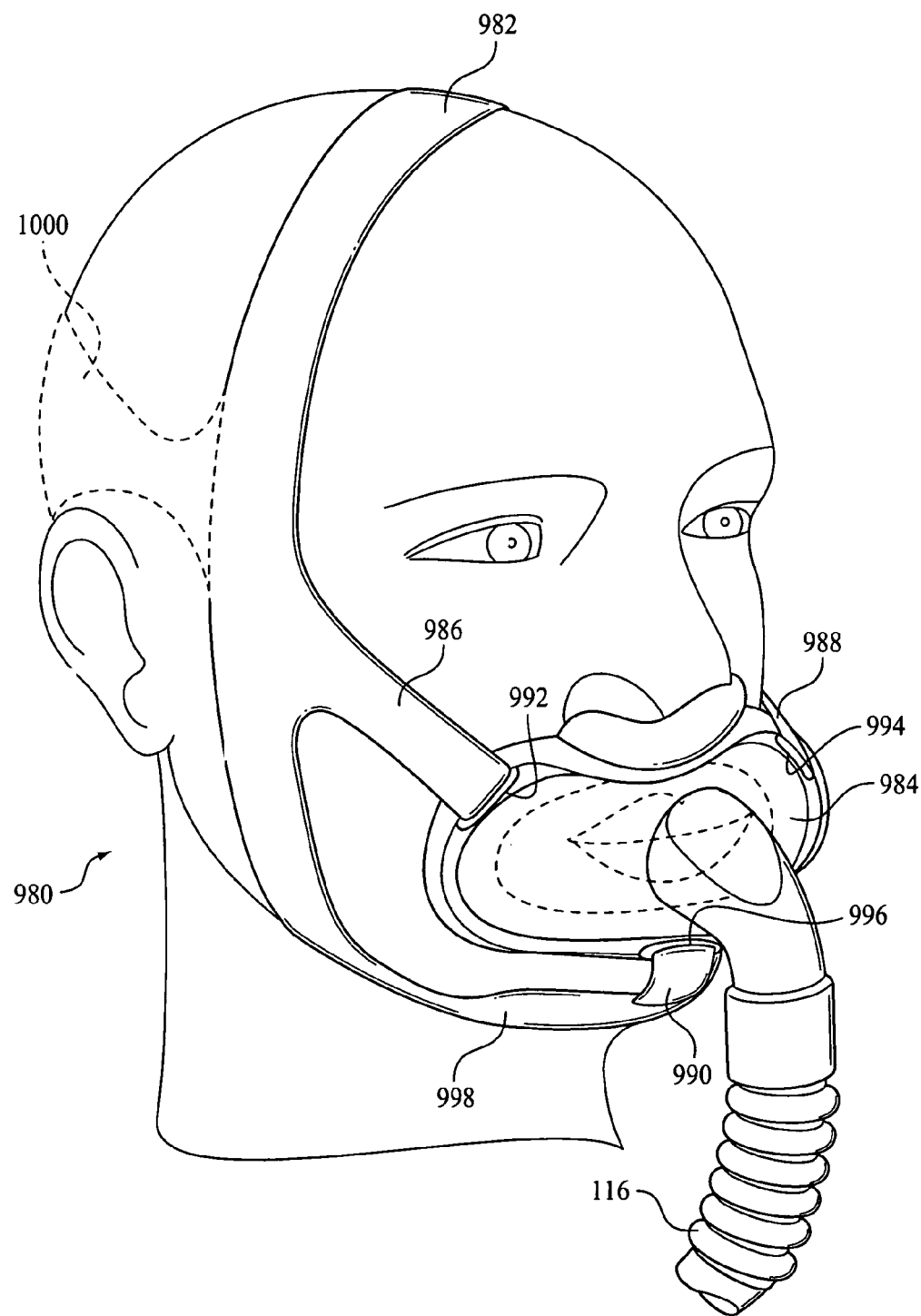

FIG. 30 illustrates an eleventh embodiment of a patient interface assembly 980 that includes a headgear 982 and a patient interface 984. In this embodiment, patient interface 984 includes a three-point attachment technique whereby three headgear straps 986, 988, and 990 are coupled to the patient interface. In this embodiment, slots 992, 994, and 996 are provided in the faceplate for receiving straps 986, 988, and 990, respectively. The lower strap 990 is connected to a chin strap 998.

This embodiment also illustrates cup-like a nasal interface portion that corresponds, for example, to nasal interface portion 124 of FIGS. 1-5. It can be appreciated that when the patient interface is worn by the user, the nasal interface portion of the seal member extends over the tip of the nose, but does not extend so far up the nose toward the eyes so as to overlie any portion of the bridge of the nose, the lowermost portion of which is indicated by reference numeral 920. The present invention contemplates that the nasal interface portion of the seal member can extend up the nose toward the eyes farther than shown in FIG. 30, so long as it does not overly the bridge of the nose.

Figure 32:
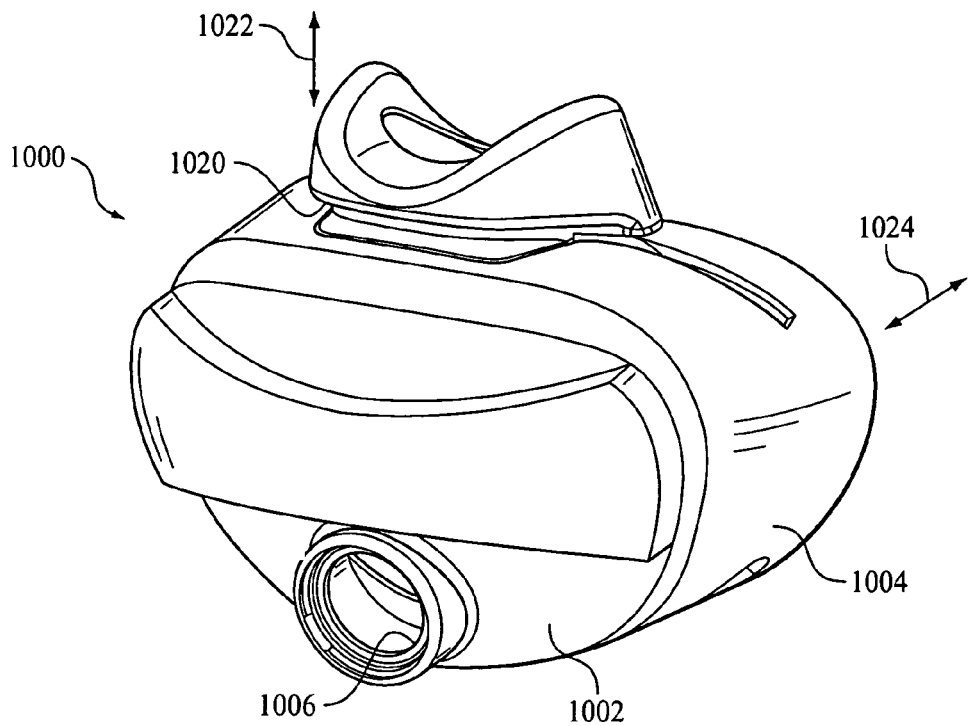
FIGS. 32-34 are front perspective, rear perspective, and cross-sectional views, respectively, of a twelfth embodiment of the patient interface according to the principles of the present invention.
Figure 33:
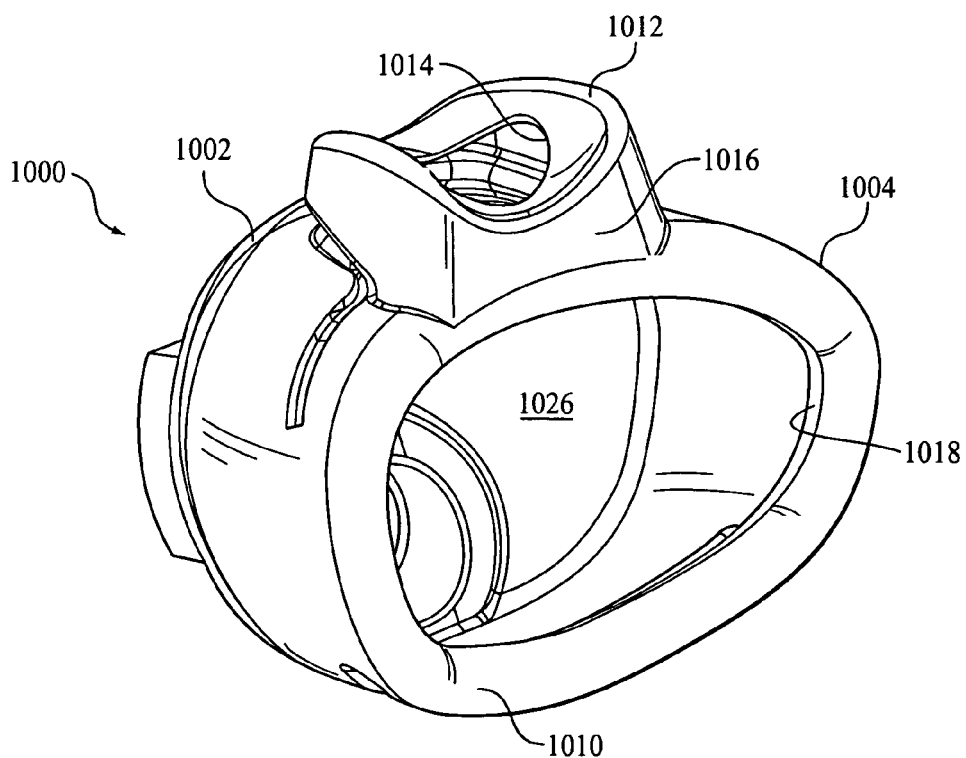
Figure 34:
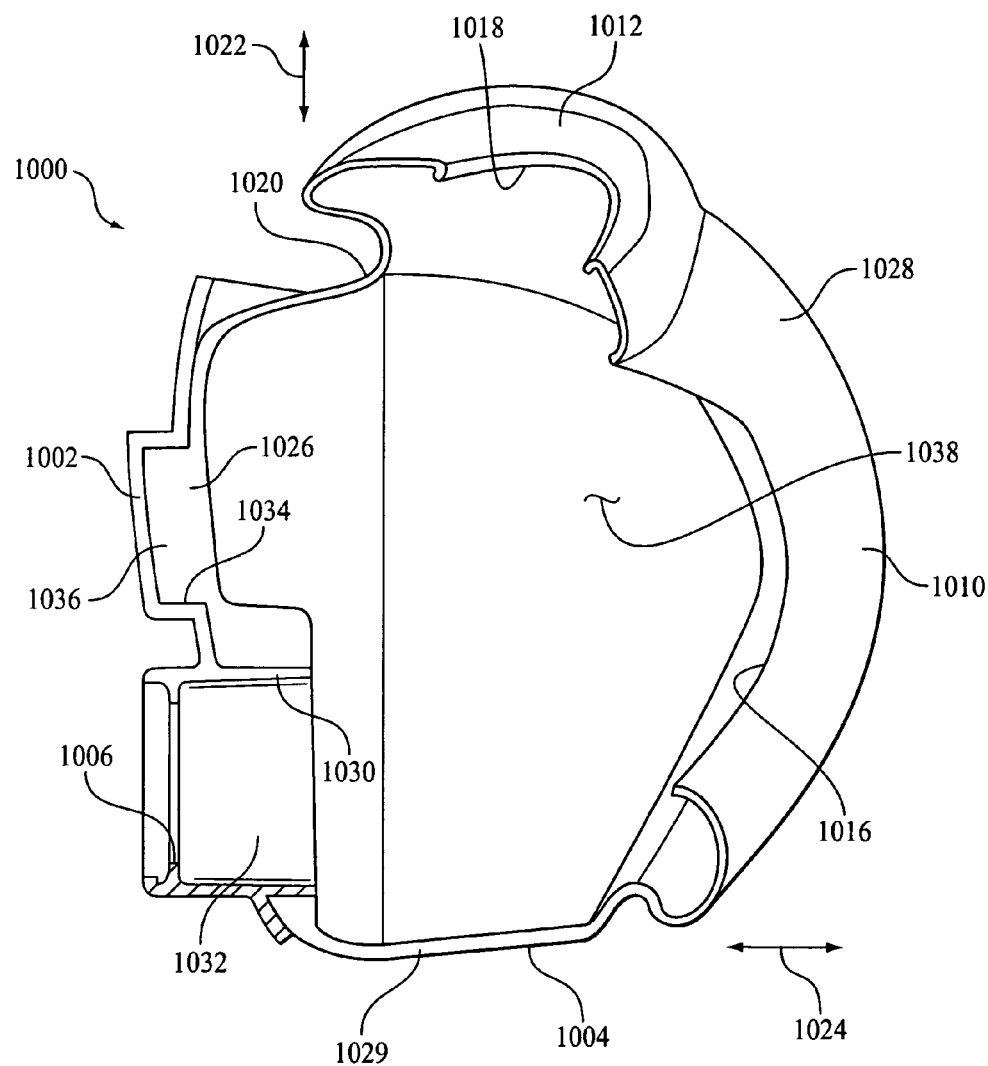

A twelfth embodiment of a patient interface 1000 is illustrated in FIGS. 32-34. Patient interface 1000 includes a faceplate 1002 and a seal member 1004 attached to the faceplate. Faceplate 1002 is a rigid or semi-rigid structure having a generally curved configuration and includes an opening or port 1006 for connecting to a patient circuit or a patient interface coupling. It should be noted that headgear attachment elements are not shown on faceplate 1002 to simplify the illustration. It is to be understood that the present invention contemplates using any suitable technique to attach the headgear to the faceplate.

As in the previous embodiments, seal member 1004 includes an oral cushion portion 1010 and a nasal interface portion 1012. Seal member 1004 is similar to the seal member shown in FIGS. 26 and 26 in that a web of material 1014 is provided between an opening 1016 in the oral cushion portion and an opening 1018 in the nasal interface portion. In this embodiment, nasal interface portion 1012 protrudes some distance from a surface of a sidewall of the oral cushion portion.

In addition, a pleat 1020 is provided in the material at the front portion of the nasal interface portion, i.e., the portion that is closer to the tip of the nose when the interface is worn by the user. Pleat 1020, in addition to enhancing the flexibility of the walls of the natal interface portion, allows the patient contacting surface of the nasal interface portion to move in a direction indicated by arrow 1022, so that nasal interface portion properly seats itself on the user. The direction indicated by arrow 1022 corresponds, in general, to a vertical direction that is generally parallel to the face of the user. On the other hand, the patient contacting portion of oral cushion portion 1004 moves in a direction generally indicated by arrow 1024, so that the oral cushion portion compresses to properly seat itself on the user. The direction indicated by arrow 1024 is generally perpendicular to direction indicated by arrow 1022. This ability for oral cushion portion 1010 and nasal interface portion 1012 to be compressed or move in different directions, while still being defined by a unitary piece of material, provides the ability of patient interface 1000 to fit a wide variety of differently sized users.

In this embodiment, as best illustrated in FIG. 34, which is a cross-sectional view of patient interface 1000, seal member 1004 is a cup-shaped member, having a wall 1026 that is distal from patient contacting portion 1028 of the oral cushion portion. Wall 1026 is generally adjacent to faceplate 1002 when the faceplate is assembled with the seal member. A sidewall 1029 extends from wall 1026 to patient contacting portion 1028. An opening 1030 is defined in wall 1026 to receive a coupling portion 1032 of faceplate 1002. In addition, a groove 1034 is defined in the faceplate and a protrusion 1036 is provided in the seal member such that the groove and the protrusion cooperate with one another to maintain the seal member and the faceplate in an assembled configuration and/ or properly oriented relative to one another. Thus, the seal member alone, i.e., without the faceplate, defines a chamber 1038 that serves as a nose receiving cavity. It is to be understood that that the present invention contemplates other techniques and configurations for coupling faceplate 1002 to seal member 1004 in addition to or in place of that shown in the figures.

The present invention also contemplate eliminating the faceplate entirely. In which case, the headgear attachment mechanism is provided directly on the seal member. In addition, the patient circuit coupling is also provided directly on the seal member. As in the previous embodiment, any suitable technique can be used to couple the headgear straps and the patient circuit directly to the seal member. Of course, portions of the seal member can be reinforced, thickened, or otherwise stiffened to support the headgear attachments and the patient circuit coupling.

Figure 35:
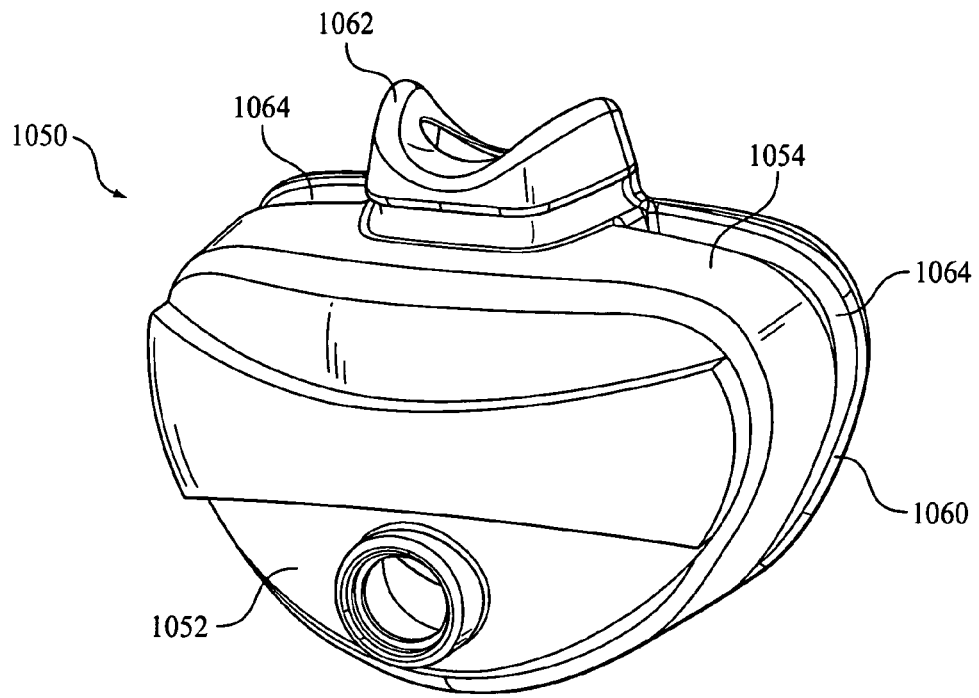
FIGS. 35 and 36 are front and rear perspective views of a thirteenth embodiment of a patient interface according to the principles of the present invention.
Figure 36:
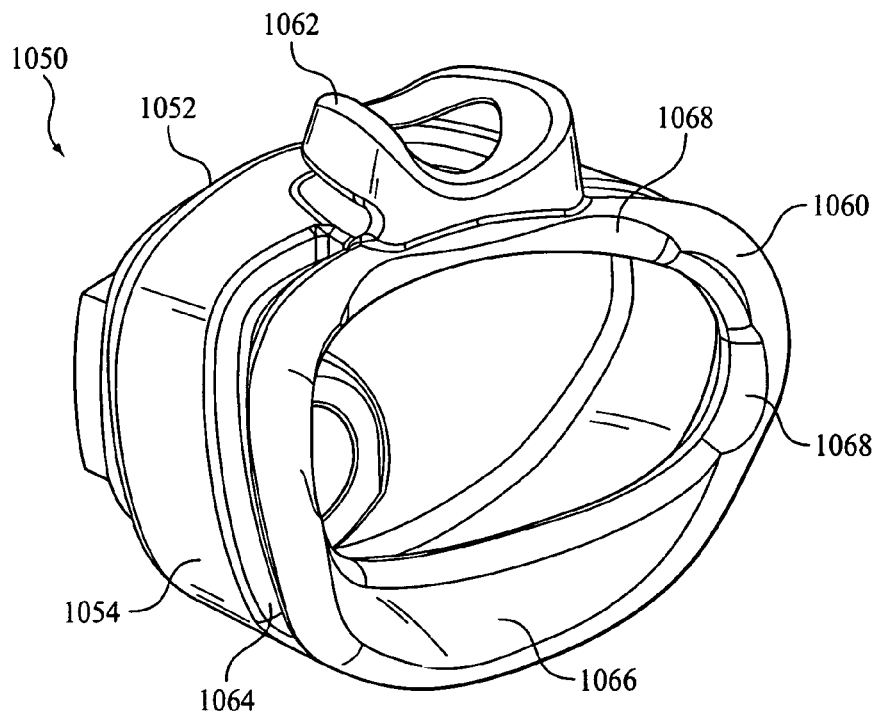

FIGS. 35 and 36 illustrate a thirteenth embodiment of the patient interface 1050 according to the principles of present invention. Patient interface 1050 includes a faceplate 1052 and a seal member 1054 attached to the faceplate. Seal member 1054 includes an oral cushion portion 1060 and a nasal interface portion 1062. In this embodiment, the seal member is generally similar to that of FIGS. 32-34, except that a groove or pleat 1064 is defined around a perimeter of oral cushion portion 1060. Groove 1064 enhances the flexibility of the seal member is a direction normal to the surface of the patient. In addition, a relatively large flap 1066 is provided in the patient contacting portion of the seal member, and, in particular, at lower portion of the oral cushion portion that is below the user's mouth when the patient interface is worn by the user. Of course, the large flap can be located at other locations along the perimeter of the seal or at multiple locations. This flap helps provided a leak resistance seal against the user. The patient contact portion of the seal member also includes angled portions 1068 to provide the desired sealing characteristics against the surface of the user.

Figure 37:
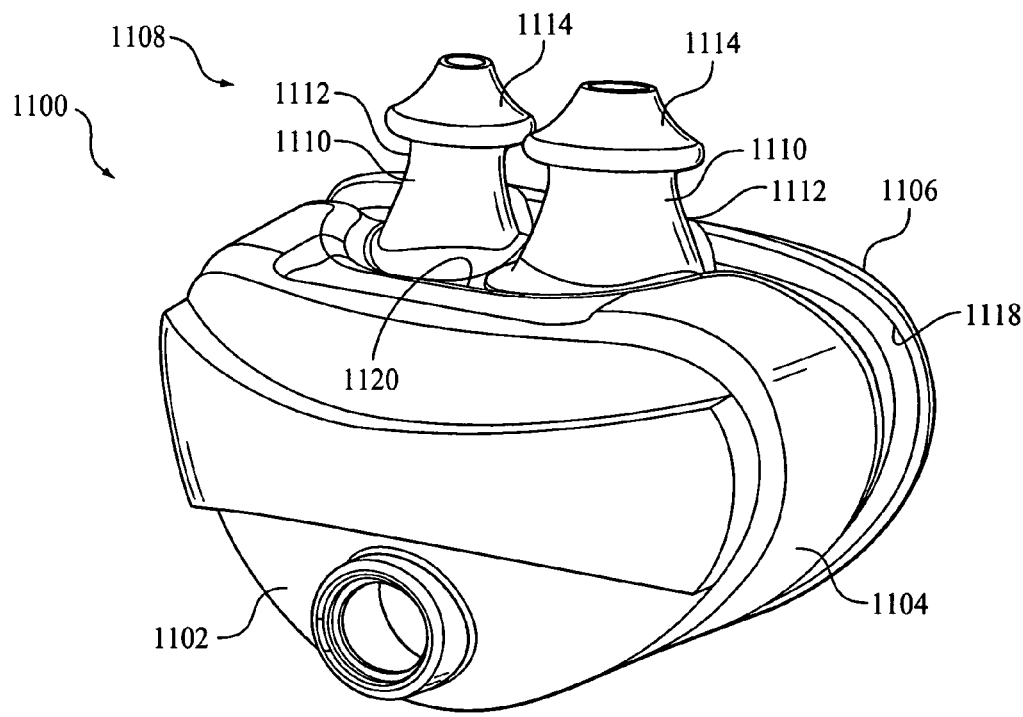
FIGS. 37 and 38 are front and rear perspective views of a fourteenth embodiment of a patient interface according to the principles of the present invention.
Figure 38:
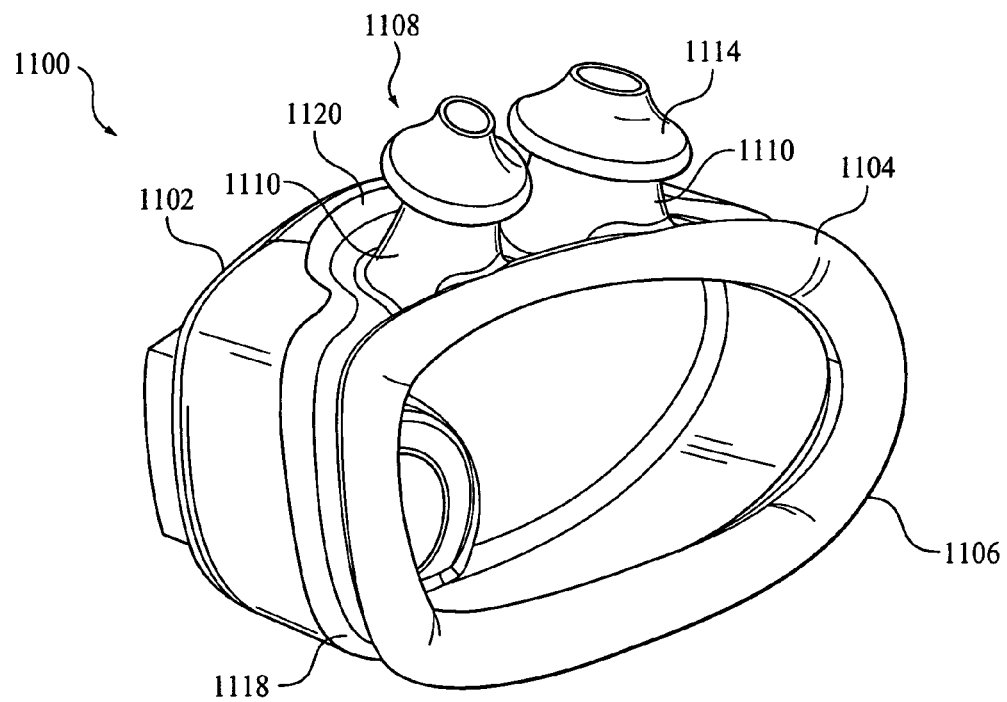

FIGS. 37 and 38 illustrate fourteenth embodiment for a patient interface 1100 having a faceplate 1102 and a seal member 1104 attached to the faceplate. Seal member 1104 includes an oral cushion portion 1106 and a nasal interface portion 1108. In this embodiment, nasal interface portion 1108 includes a pair of nasal pillows or prongs 1110, each of which extends from the oral cushion portion of the seal member. The nasal prongs in this embodiment include a stem portion 1112 and an interface portion 1114 disposed at the end of the stem portion. An opening 1116 is defined in the interface portion of the nasal prong. The stem portion is sufficiently flexible so that the nasal prong can move to fit a variety of differently sized patients. In this embodiment, a groove or pleat 1118 is provided around the perimeter of the oral cushion portion. Groove 1118 also extends around the nasal interface portion of the seal member, as indicated by reference numeral 1120.

Figure 39:
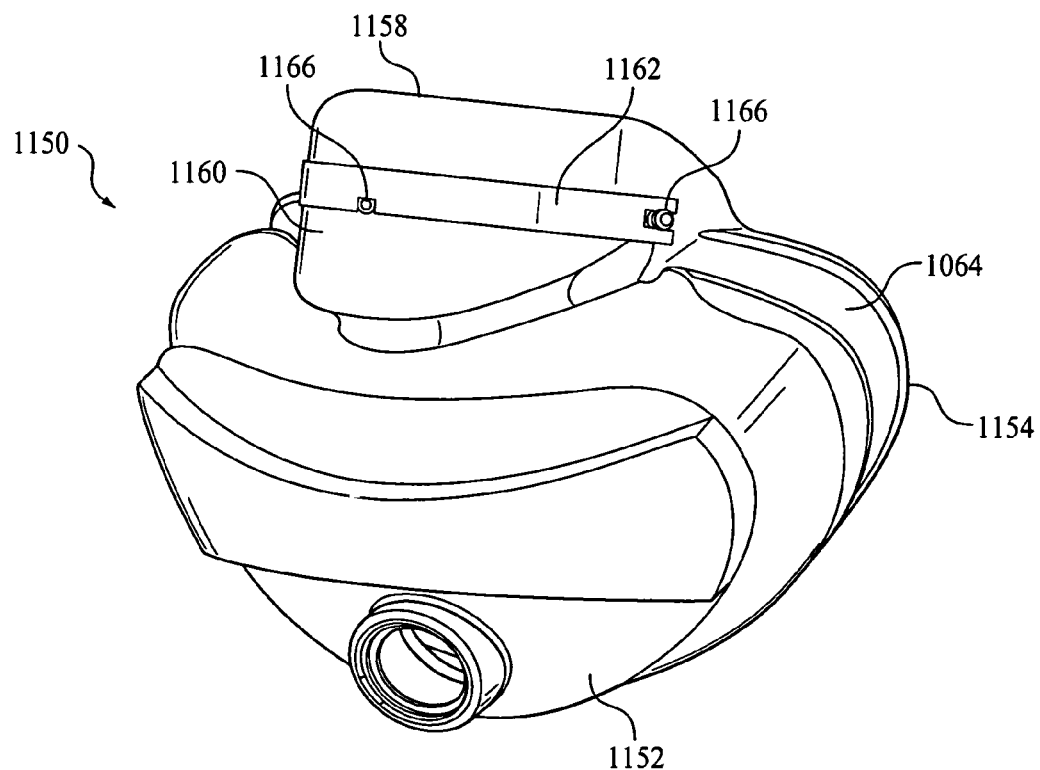
FIGS. 39-41 are front perspective, rear perspective, and exploded views, respectively, of a fifteenth embodiment of a patient interface according to the principles of the present invention.
Figure 40:
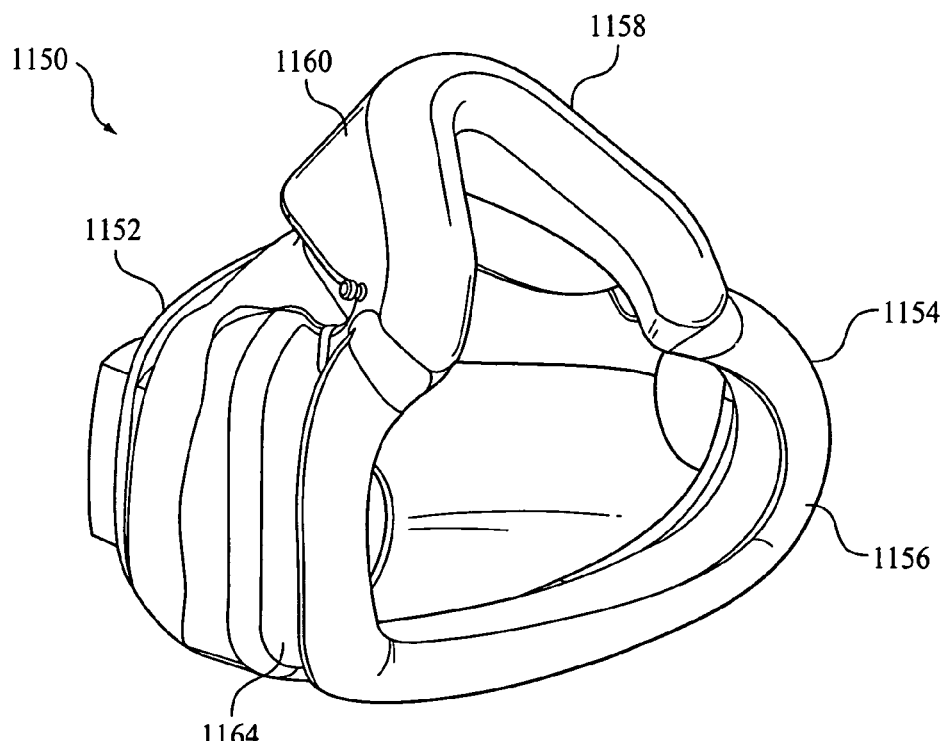
Figure 41:
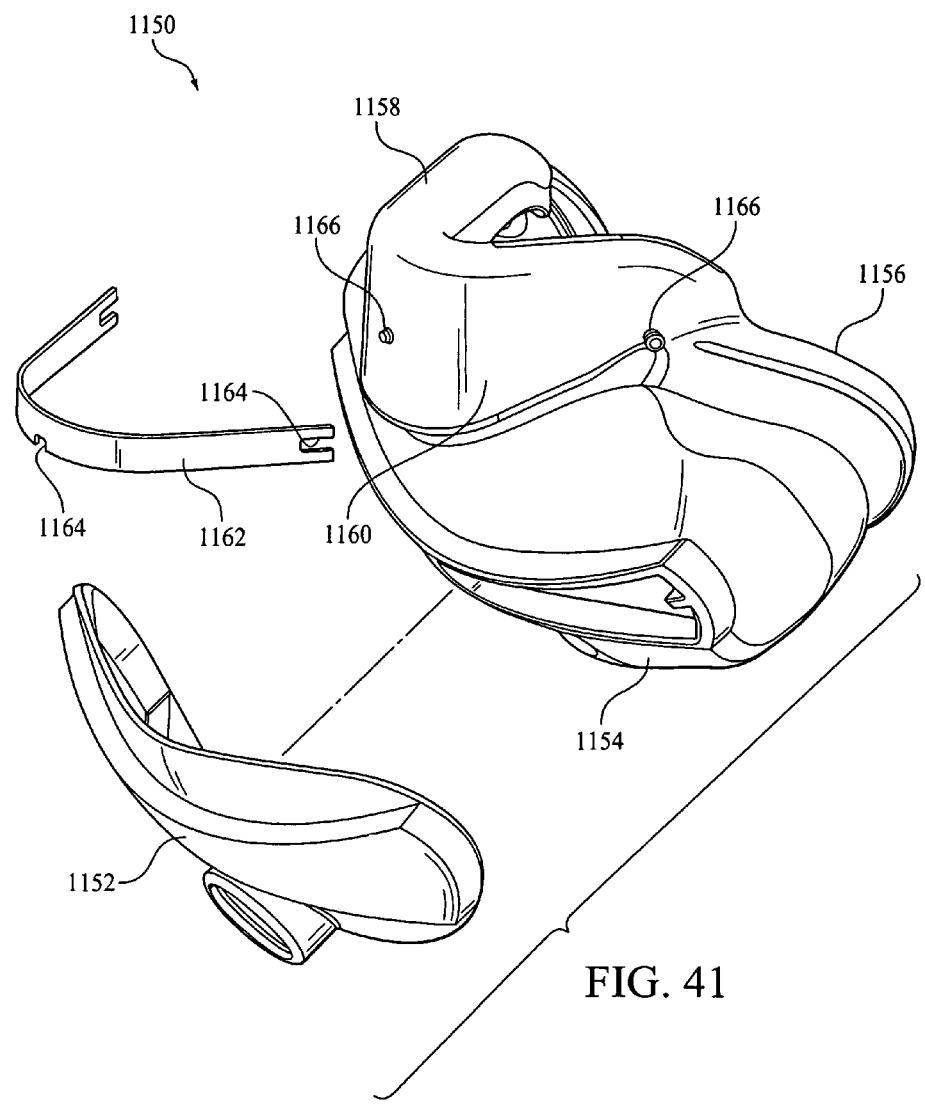

FIGS. 39-41 illustrate a fifteenth embodiment of a patient interface 1150 having a faceplate 1152 and a seal member 1154 attached to the faceplate. Seal member 1154 includes an oral cushion portion 1156 and a nasal interface portion 1158. The nasal interface portion of the seal member is structurally similar to that shown in FIGS. 1-7 18-22 and includes a flexible peripheral wall 1160 extending from the oral cushion portion of the seal member. Nasal interface portion 1158 also includes a rigid or semi-rigid band 1162 that is attached to wall 1160. In exemplary embodiment, band 1162 is capable of being bent (inward or outward) and is capable of retaining the new shape upon being bent, so that the nasal interface portion can be configured to particular anatomical attributes of the user.

The present invention contemplates attaching band 1162 to wall 1160 using any suitable technique, including permanently or removeably mounting the band on the wall. A permanent attachment can be achieved by adhering the band to the wall. A removeable attachment is shown in FIGS. 39-41. A removeable attachment allows different bands, for example bands having different sizes, stiffnesses, or degrees of flexibility, to be used with the nasal interface portion. In the illustrated embodiment, band 1162 includes notches 1164 that attach to protrusions 1166 provided on wall 1160.

Figure 42:
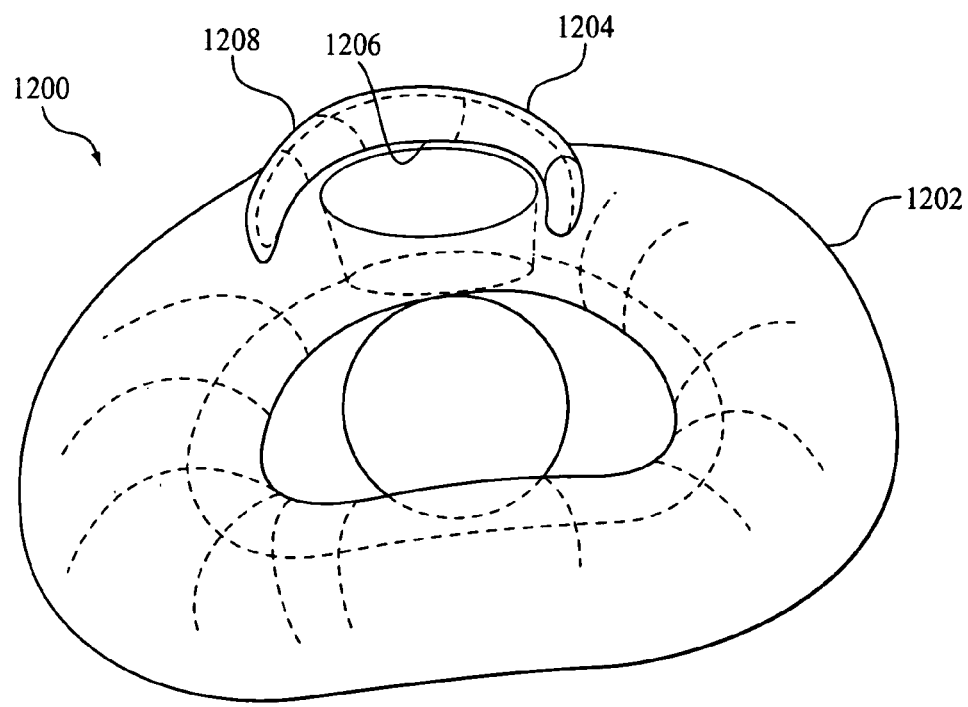
FIG. 42 is a perspective views of a sixteenth embodiment of a seal member according the principles of the present invention.

FIG. 42 illustrates a sixteenth embodiment of a seal member 1200 suitable for use in the patient interface of the present invention. Seal member 1200 includes an oral cushion portion 1202 and a nasal interface portion 1204. The oral cushion portion of the seal member is a gas-filled bladder. The nasal interface portion is defined by a single opening 1206 that extends through the gas-filled bladder. An optional flap 1208 is provided around at least a portion of opening 1206 to help seal the nasal interface portion around the nasal passages of the user. It is to be understood that the present invention contemplates that the bladder can be filled, in whole or in part, with other materials, such as a gel or foam.

Figure 43:
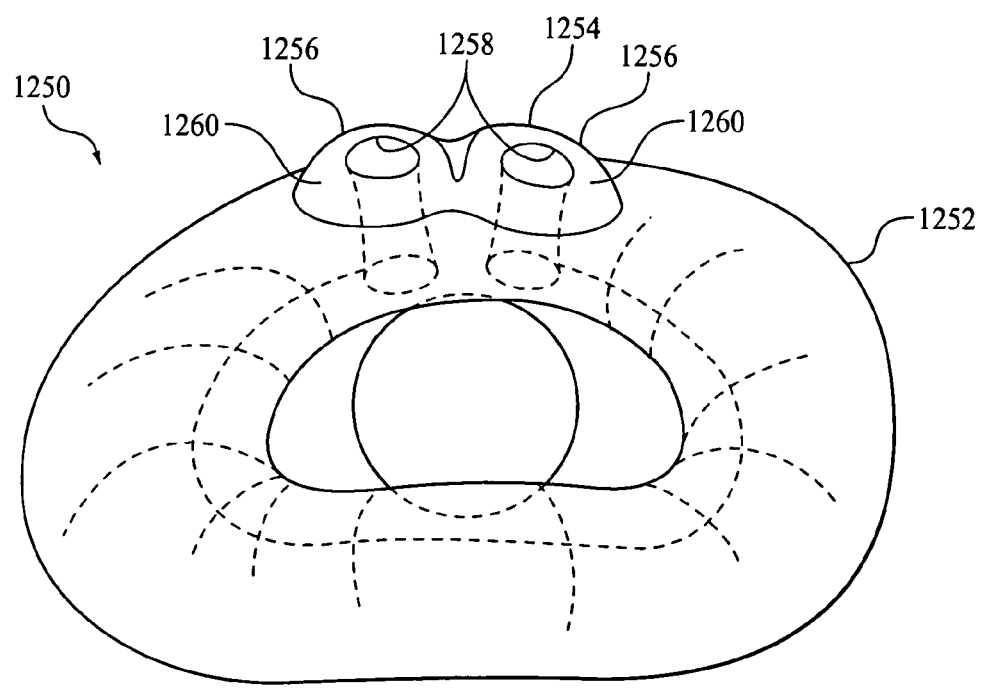
FIG. 43 is a perspective views of an seventeenth embodiment of a seal member according the principles of the present invention.

FIG. 43 illustrates a seventeenth embodiment of a seal member 1250 according the principles of the present invention. Seal member 1200 includes an oral cushion portion 1252 and a nasal interface portion 1254. The oral cushion portion of the seal member, as in the embodiment of FIG. 42, is a gas-filled bladder. In this embodiment, however, the nasal interface portion is defined by a pair of nasal prongs 1256, each of which includes an opening 1258 that extends through the gas-filled bladder. Each nasal prong includes a protrusion or bulbous portion 1260. In an exemplary embodiment, the bulbous portion is defined by the material forming the gas-filled bladder.

Figure 44:
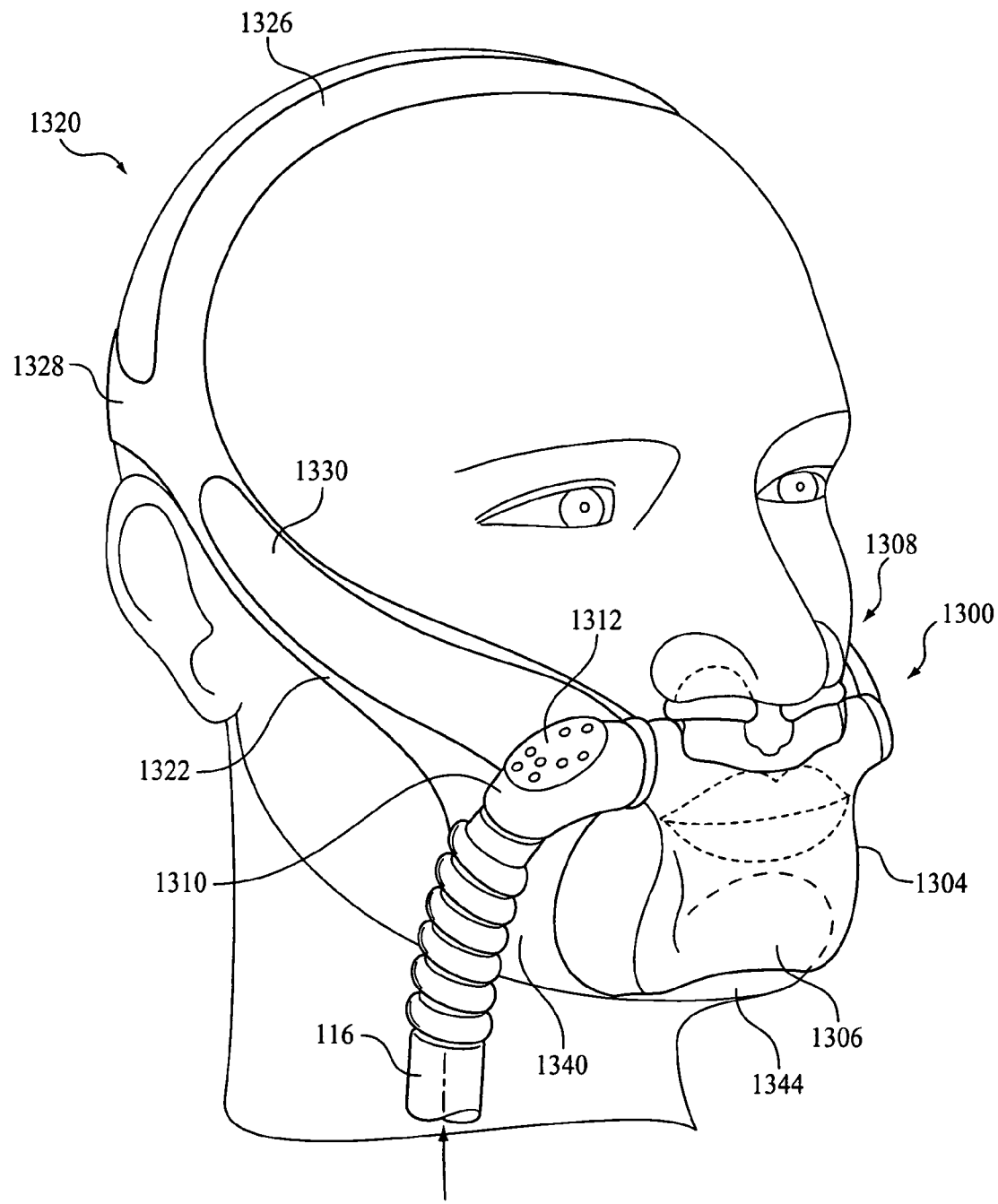
FIG. 44 is a perspective view of an eighteenth embodiment of a patient interface according to the principles of the present invention shown being worn by a user.
Figure 45:
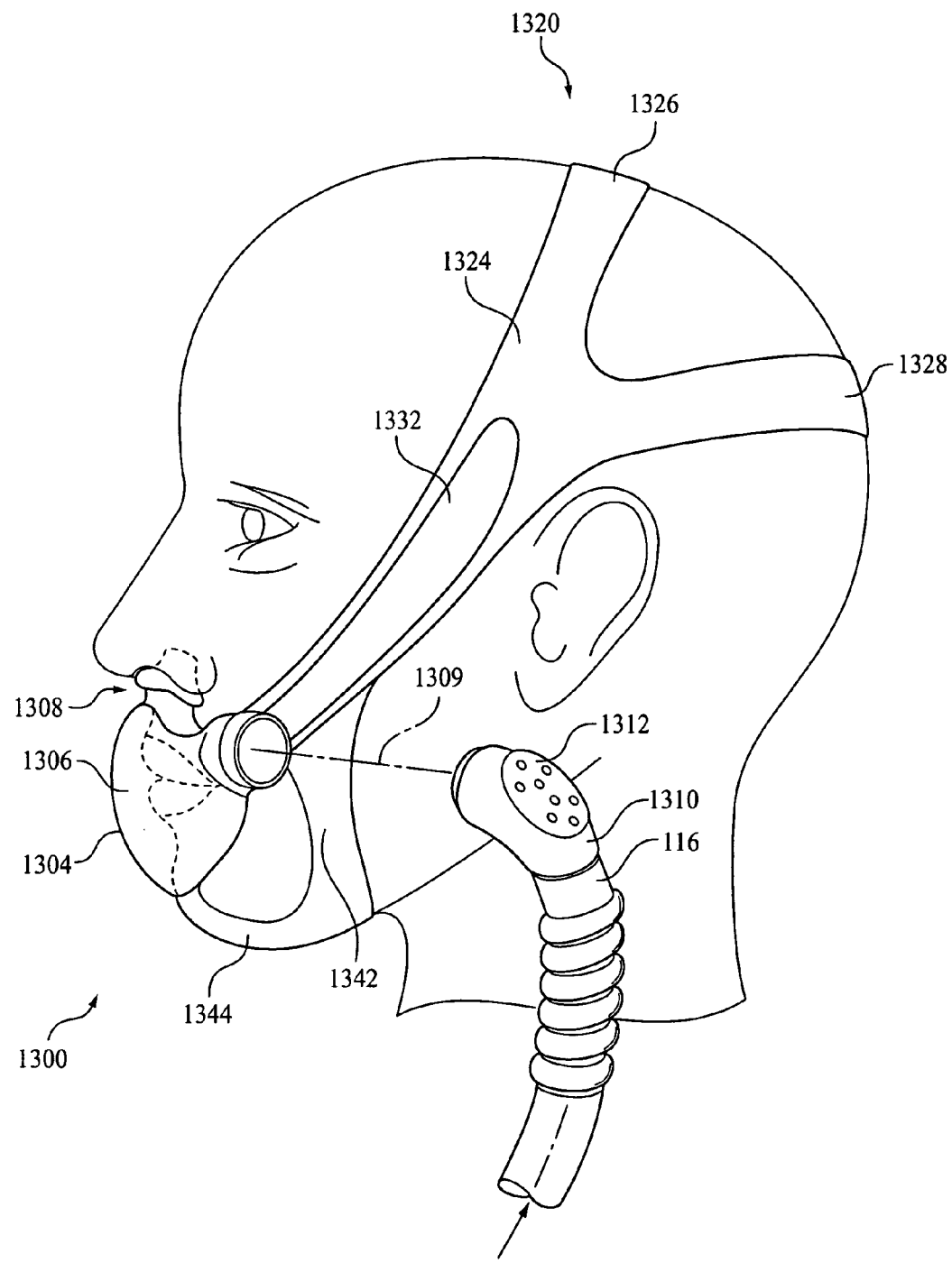
FIG. 45 is a side view of the patient interface of FIG. 44.

FIGS. 44 and 45 illustrate an eighteenth embodiment of a patient interface 1300 according to the principles of the present invention shown worn by a user. Patient interface 1300 includes a seal member 1304 having an oral cushion portion 1306 and a nasal interface portion 1308. A coupling 1310 is rotatably attached to one side of seal member 1310 to connect conduit 116 to the patient interface. Coupling 1310 can be permanently coupled to the seal member or selectively coupled, as indicated by arrow 1309 in FIG. 45. The present invention also contemplates that the conduit can be attached to the seal member at other locations or at more than one location. An exhaust vent assembly 1312 is provided on coupling 1310. Conduit 116 can be fixed or rotatably attached to coupling 116.

Nasal interface portion 1308, in this exemplary embodiment, is a pair of pillows/prongs, each of which extends from the oral cushion portion of the seal member. Similar prongs are illustrated in FIGS. 37 and 38. Of course, any of the nasal interface portions can be used in seal member 1310. Oral cushion portion 1306 extends around the mouth and down toward the user's chin. In an exemplary embodiment, the oral cushion portion is formed from a flexible or semi-rigid material or combination of materials.

A headgear assembly, generally indicated at 1320, couples patient interface 1300 to the user. In this exemplary embodiment, the headgear assembly includes a pair of straps 1322, 1324 that extend from each side of patient interface 1300. Two coupling members 1326 and 1328 are coupled to straps 1322 and 1324 and extend around the head of the user. The length of straps 1322, 1324 and/or coupling members 1326 can be adjusted to fit the headgear on a variety of differently sized heads. The present invention further contemplates providing stiffening members 1330 and 1332 coupled to straps 1322 and 1324. Stiffening members 1330 and 1332 can have any suitable configurations, can be formed from multiple components, can be shaped or curved to match or conform to the surface of the user, can be made from any suitable material or combination of materials, and may be disposed over or provided within the material forming the straps. In addition, suitable stiffening member can also be coupled to coupling members 1326 and 1328.

Headgear assembly 1330 also includes various components for securing interface 1300 to the chin or mandible of the user. In this illustrated exemplary embodiment, a pair of side straps 1340, 1342 and a chin strap 1344 are connected to oral cushion portion 1306 of seal member 1304. Chin strap 1344 extends down generally from the center of the oral cushion portion along the midline of the user over the chin and under the mandible. Side straps 1340, 1342 extend from straps 1322, 1324 along the sides of the fact and join the chin strap under the mandible. The present invention contemplates that straps 1340, 1342, and 1344 are formed from a flexible, stretchable material. Of course, other materials, including rigid or semi-rigid structures can be provided.

Figure 46:
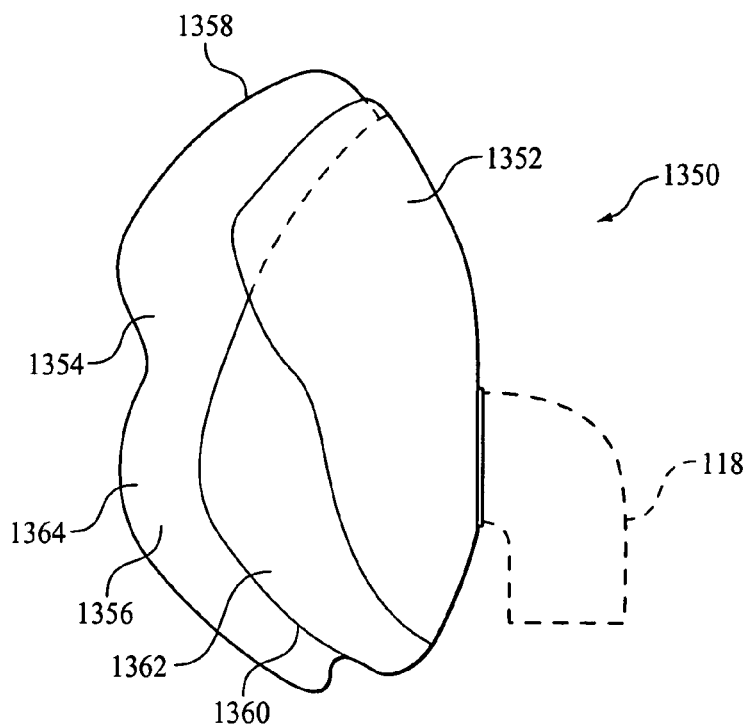
FIG. 46 is a side view of a nineteenth embodiment of a patient interface according to the principles of the present invention.

FIG. 46 is a side view of a nineteenth embodiment of a patient interface 1350 having a faceplate 1352 and a seal member 1354 attached to the faceplate. Seal member 1354 includes an oral cushion portion 1356 and a nasal interface portion 1358. In this embodiment, seal member 1354 includes at least one groove or pleat 1360 defined proximate to the portion of the seal member that contacts the user. An example of a groove or multiple grooves suitable for use in the present invention, and, in particular, the present embodiment, is disclosed in the '026 application. The present invention also contemplates forming a portion of seal member 1354 with a gel material to maximize patient comfort. A portion of the seal member that contacts the user is formed form a soft, compliant material, such as silicon.

Figure 47:
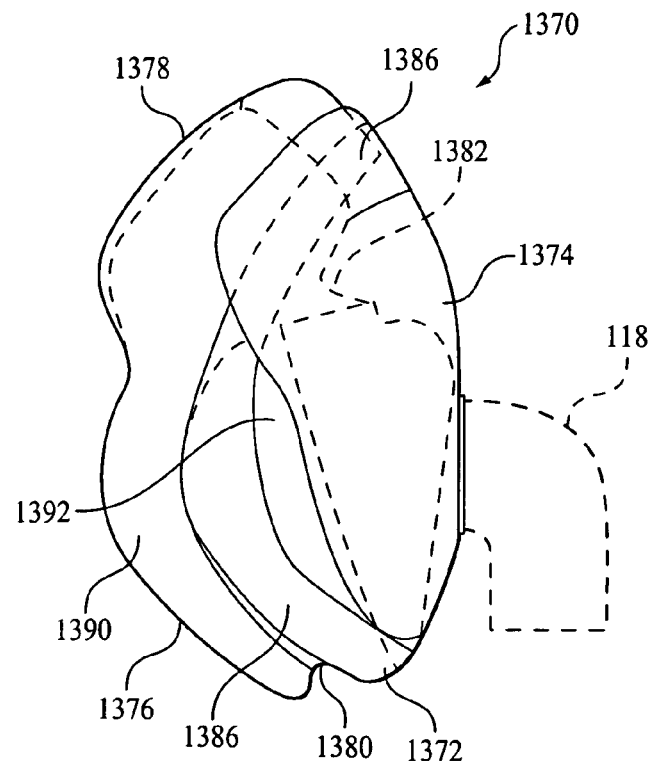
FIG. 47 is a side view of a twentieth embodiment of a patient interface according to the principles of the present invention.
Figure 48:
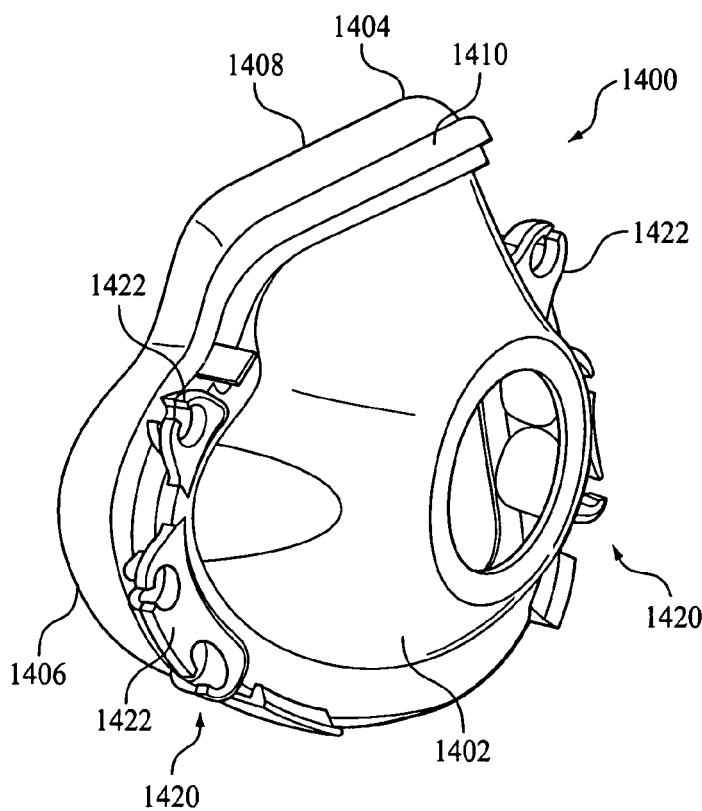
FIG. 48 is a perspective view of a twenty-first embodiment of a patient interface according to the principles of the present invention.
Figure 49:
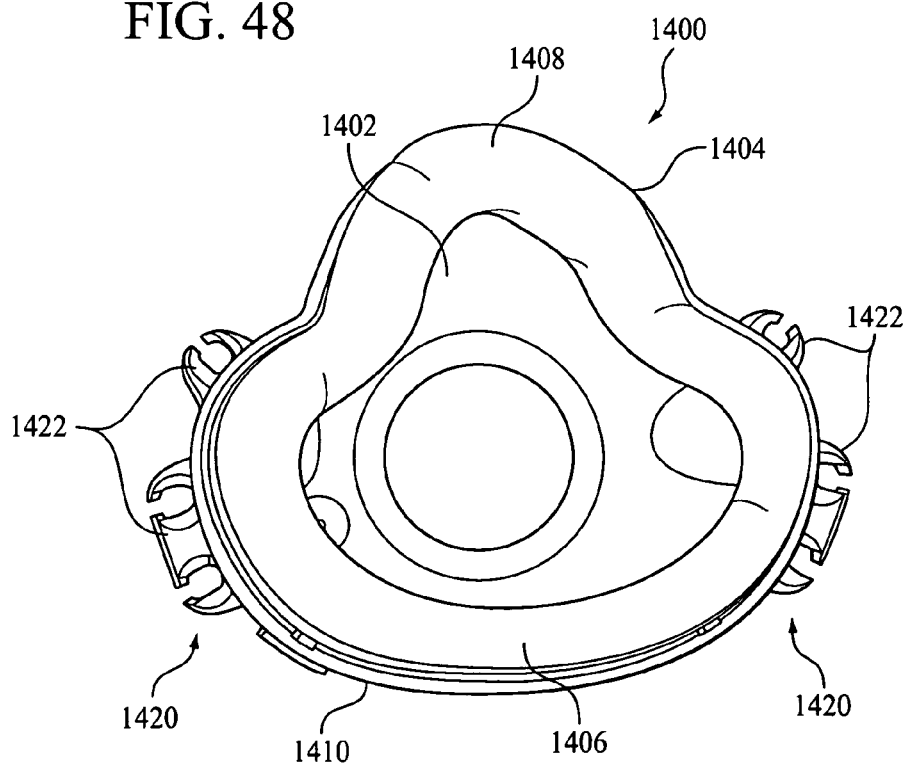
FIG. 49 is a rear view of the patient interface of FIG. 48.
Figure 50:
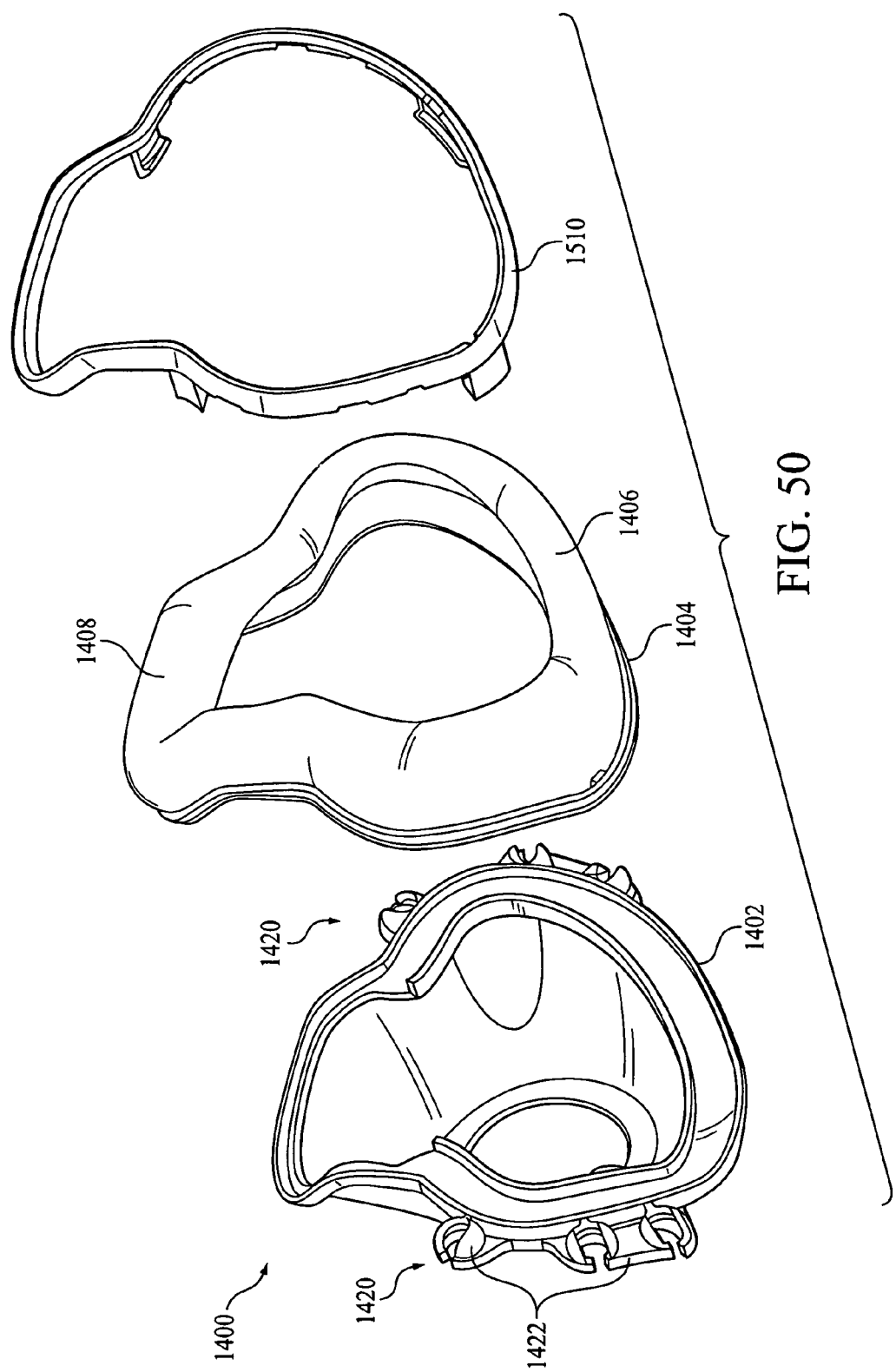
FIG. 50 is an exploded view of the patient interface of FIG. 48.

FIG. 47 illustrates a twentieth embodiment of a patient interface 1370 having a faceplate 1374 and a seal member 1372 attached to the faceplate. Seal member 1372 includes an oral cushion portion 1376 and a nasal interface portion 1378. In this embodiment, the seal member includes multiple grooves or pleats 1380, 1382 An example of a groove or multiple grooves suitable for use in the present invention, and, in particular, the present embodiment, is disclosed in the '026 application. The present invention also contemplates forming a portion 1386 of seal member 1374 with a gel material to maximize patient comfort. In this embodiment, unlike that of FIG. 46, gel portion 1386 is smaller and is provided as a layer or components of the larger seal member. The portion 1390 of the seal member that contacts the user is formed form a soft, compliant material, such as silicon. A base portion 1392 of the cushion contacts faceplate 1374. This portion can be formed from any suitable substance that will support both gel layer 1386 and the distal flap portion is also formed from FIGS. 48-50 illustrate a twenty-first embodiment of a patient interface 1400 having a faceplate 1402 and a seal member 1404 attached to the faceplate. Seal member 1404 includes an oral cushion portion 1406 and a nasal interface portion 1408. Faceplate 1402 and seal member 1404 are joined or coupled together via a mounting ring 1410. Of course, other techniques for selectively or permanently joining the faceplate and seal member, such as providing a tongue and groove in these components in addition to or in place of the mounting ring, are contemplated by the present invention.

In the presently illustrated embodiment, a headgear coupling assembly 1420 is provided on each side of the faceplate. More specifically, headgear coupling assembly 1420 includes sockets 1422 that correspond to the socket portion a portion of a ball-and-socket headgear attachment technique, as discussed above and as disclosed, for example, in the '179 patent. Multiple sockets are provided so that the user can select which sockets to use to connect to the ball portion of the headgear clip. Of course, more or less sockets can be provided. In addition, sockets 1422 can be provided at different locations on the faceplate or have other configurations. Indeed, the present invention contemplates using any headgear attachment element to couple the headgear strap to the patient interface, and, in particular, the faceplate.

Figure 51:
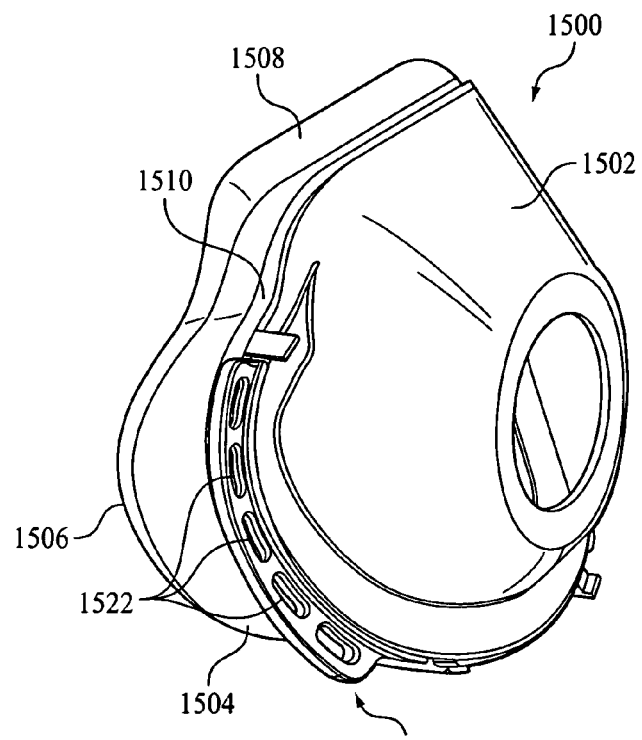
FIG. 51 is a perspective view of a twenty-second embodiment of a patient interface according to the principles of the present invention.
Figure 52:
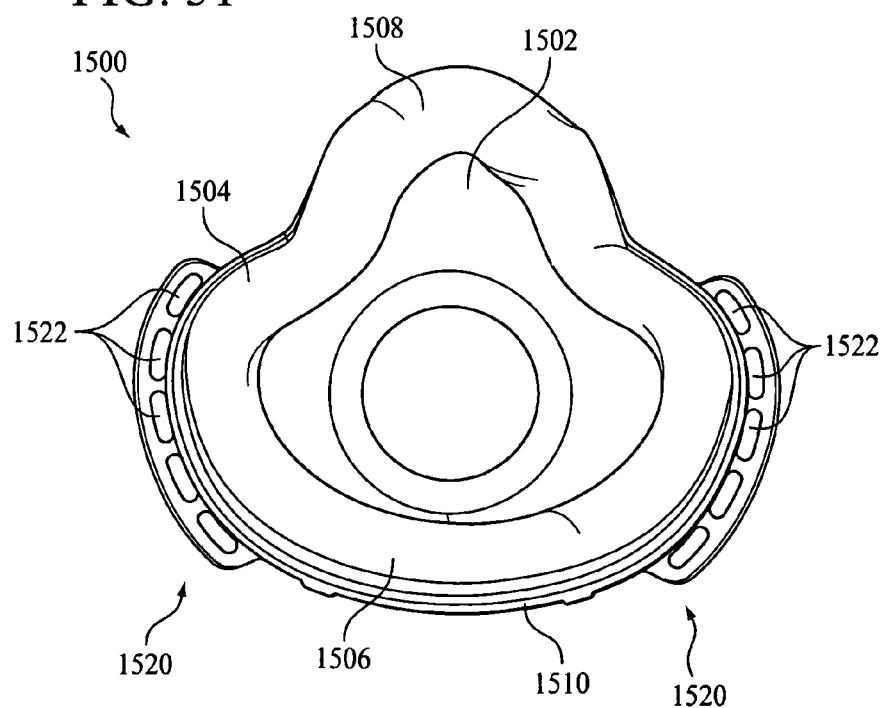
FIG. 52 is a rear view of the patient interface of FIG. 51.

FIGS. 51-53 illustrate a twenty-second embodiment of a patient interface 1500 having a faceplate 1502 and a seal member 1504 attached to the faceplate. Seal member 1504 includes an oral cushion portion 1506 and a nasal interface portion 1508. Faceplate 1502 and seal member 1504 are joined or coupled together via a mounting ring 1510. Of course, other techniques for selectively or permanently joining the faceplate and seal member, such as providing a tongue and groove in these components in addition to or in place of the mounting ring, are contemplated by the present invention.

This embodiment illustrates an example of another variation for a headgear coupling assembly 1520 associated with faceplate 1502. Headgear coupling assembly 1520 is generally similar to that shown in use with the patient interfaces illustrated in FIGS. 8-11. Each headgear coupling assembly includes a plurality of openings 1522 that are used to attach headgear clips to the faceplate. As noted above, an example of a headgear clip that can be attached to headgear coupling assembly 1520 are hook clips 340, as shown for example, in FIGS. 13-14. Of course, the configuration for headgear coupling assemblies 1520 and openings 1522 can be varied so long as the function of providing an attachment structure for securing a headgear to the patient interface is accomplished.

The present invention contemplates that features known in the art for use with cushions, faceplates, and masks in general, can be used with the patient interface embodiments of the present invention. For example, it is known to provide reinforcing structures in a seal member to support all or portions of the seal member. Examples of such reinforcing portions are ribs coupled to the seal member and rigid or semi-rigid materials defined in the seal member or disposed adjacent to the seal member. It is also known to provide multiple flaps generally at the distal portion of the seal member, which is the portion that contacts the user. See, e.g., U.S. Pat. No. 4,971,451. This multiple flap configuration can be used with the seal member of the present invention.

The present invention further contemplates that patient interface coupling 118 is any device capable of attaching the patient interface to a patient circuit. It can be a simple conduit or it can include additional features, such as exhalation ports, entrainment valve, quick release mechanisms, or any combination thereof. Examples of patient interface couplings suitable for use in the present invention are disclosed in U.S. Pat. Nos. 6,851,425; 5,647,355; and 5,438,981 the contents of each of which are incorporated herein by reference. U.S. patent application Ser. No. 11/312,027 also teaches patient interface couplings suitable for use in the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:
1. A patient interface comprising:
   (a) a seal member adapted to contact a face of a user to provide a sealed interface with such a user, wherein the seal member comprises:
      (1) an oral cushion portion adapted to provide a sealed interface with such a user, wherein a sealing of the oral cushion portion at least partially surrounds a mouth of such a user,
      (2) a pleat provided at a portion the perimeter of the oral cushion portion, and

(3) a nasal interface portion operatively coupled to the oral cushion portion, wherein the nasal interface portion is adapted to form a sealed interface with nares of such as user; and (b) a faceplate, wherein the seal member is operatively attached to the faceplate.

2. The patient interface of claim 1, wherein the pleat fully surrounds the perimeter of the oral cushion portion.

3. The patient interface of claim 1, wherein the oral cushion portion includes a first sidewall disposed on a first each side of a face of a user and a second sidewall disposed on a second each side of a face of a user opposite the first side responsive to the patient interface being donned by a user, wherein the pleat includes a first pleat disposed in the first sidewall and a second pleat dispose din the second sidewall, and wherein the first pleat is separate from the second pleat.

4. The patient interface of claim 1, wherein the nasal interface portion comprises a protrusion that extends from the oral cushion portion, and wherein the protrusion is sized and configured that the protrusion is bounded at its upper extremity by a lower end of a nose of such a user.

5. The patient interface of claim 1, wherein the nasal interface portion comprises is a nasal cup or a pair of nasal pillows.

6. The patient interface of claim 1, wherein the nasal interface portion comprises is a pair of nasal pillows, and wherein the nasal pillows both have a generally concave exterior shape.

7. The patient interface of claim 1, wherein the oral cushion portion includes a first end portion, a second end portion adapted to contact a surface of a user, and a wall extending between the first end portion and the second end portion, and wherein the pleat is disposed in at portion of the wall.

8. The patient interface of claim 1, wherein the oral cushion portion comprises a bladder having an interior.

9. The patient interface of claim 8, wherein the interior of the bladder is gas-filled or gel-filled.

10. The patient interface of claim 1, wherein a first opening is defined in the oral cushion portion to provide a seal around such a user's mouth and a second opening is defined in the nasal interface portion to provide a seal around at least one of such a user's nares.

11. The patient interface of claim 1, wherein the oral cushion portion is generally oval shaped.

12. The patient interface of claim 1, further comprising a reinforcing member associated with the oral cushion portion, the nasal interface portion, or both to provide structural support for an associated portion of the seal member.

13. The patient interface of claim 1, further comprising means for selectively attaching the seal member to the faceplate.

14. The patient interface of claim 1, further comprising a headgear coupled to the faceplate.

15. The patient interface of claim 1, further comprising a conduit coupled to the faceplate, wherein the conduit is adapted to carry a flow of gas to an interior chamber defined by the seal member.

16. The patient interface of claim 15, wherein the conduit is coupled to a first side of the faceplate.

17. The patient interface of claim 15, wherein the conduit is rotatably coupled to the faceplate.

18. A patient interface comprising:
(a) a seal member adapted to contact a face of a user to provide a sealed interface with such a user, wherein the seal member comprises:
(1) an oral cushion portion adapted to provide a sealed interface with such a user, wherein a sealing of the oral cushion portion at least partially surrounds a mouth of such a user, and
(2) a nasal interface portion operatively coupled to the oral cushion portion, wherein the nasal interface portion is adapted to form a sealed interface with nares of such as user;
(b) a faceplate, wherein the seal member is operatively attached to the faceplate,
(c) a conduit rotatably coupled to a first side of the faceplate, wherein the conduit is adapted to carry a flow of gas to an interior chamber defined by the seal member.

19. The patient interface of claim 18, wherein the nasal interface portion comprises a protrusion that extends from the oral cushion portion, and wherein the protrusion is sized and configured that the protrusion is bounded at its upper extremity by a lower end of a nose of such a user.

20. The patient interface of claim 18, wherein the nasal interface portion comprises is a nasal cup or a pair of nasal pillows.

* * * * *